(12) United States Patent
McDermott

(10) Patent No.: US 11,504,280 B2
(45) Date of Patent: Nov. 22, 2022

(54) INCONTINENCE CARE SYSTEM AND METHOD THEREFOR

(71) Applicant: CARE CHANGER INC., Victoria (CA)

(72) Inventor: Jim McDermott, Victoria (CA)

(73) Assignee: CARE CHANGER INC., Victoria (CA)

( * ) Notice: Subject to any disclaimer, the term of this patent is extended or adjusted under 35 U.S.C. 154(b) by 138 days.

(21) Appl. No.: 16/648,633

(22) PCT Filed: Sep. 18, 2018

(86) PCT No.: PCT/CA2018/051164
§ 371 (c)(1),
(2) Date: Mar. 18, 2020

(87) PCT Pub. No.: WO2019/056096
PCT Pub. Date: Mar. 28, 2019

(65) Prior Publication Data
US 2020/0281777 A1    Sep. 10, 2020

Related U.S. Application Data

(60) Provisional application No. 62/560,390, filed on Sep. 19, 2017.

(51) Int. Cl.
*A61F 13/42* (2006.01)
*G01K 3/10* (2006.01)
(Continued)

(52) U.S. Cl.
CPC ............ *A61F 13/42* (2013.01); *A61B 5/0002* (2013.01); *A61B 5/0008* (2013.01); *A61B 5/01* (2013.01);
(Continued)

(58) Field of Classification Search
None
See application file for complete search history.

(56) References Cited

U.S. PATENT DOCUMENTS

2005/0245839 A1* 11/2005 Stivoric ............... A61B 5/0008
600/549
2006/0258916 A1* 11/2006 Pietersen ............. A61B 5/6804
600/301
(Continued)

FOREIGN PATENT DOCUMENTS

CA    2876622 A1    2/2013
CA    2969780 A1    6/2016
(Continued)

OTHER PUBLICATIONS

IPRP 12232019, International Preliminary Report on Patentability cited in corresponding International PCT App No. PCT/CA2018/051164; dated Dec. 23, 2019; 5 pp.
(Continued)

*Primary Examiner* — John F Mortell
(74) *Attorney, Agent, or Firm* — Lempia Summerfield Katz LLC

(57) ABSTRACT

A system and a method of detecting a voiding event of a care-receiver uses a temperature sensor for measuring temperatures in real-time at a location adjacent a lower portion of the care-receiver's torso where the voiding event is to occur. The system and method then determines the voiding event based on the measured temperatures.

20 Claims, 16 Drawing Sheets

(51) Int. Cl.
  *A61B 5/01* (2006.01)
  *A61B 5/00* (2006.01)
  *G01G 19/44* (2006.01)
  *G01K 13/00* (2021.01)
  *A61B 5/20* (2006.01)

(52) U.S. Cl.
  CPC .............. *A61B 5/202* (2013.01); *A61B 5/746* (2013.01); *G01G 19/445* (2013.01); *G01K 3/10* (2013.01); *G01K 13/00* (2013.01); *A61F 2013/424* (2013.01)

(56) References Cited

U.S. PATENT DOCUMENTS

| | | | | |
|---|---|---|---|---|
| 2007/0270774 | A1* | 11/2007 | Bergman | G16H 40/60 604/361 |
| 2010/0164733 | A1* | 7/2010 | Ales | A61F 13/42 340/604 |
| 2011/0060300 | A1* | 3/2011 | Weig | A61M 1/0003 604/319 |
| 2012/0245542 | A1* | 9/2012 | Suzuki | A61F 13/42 604/319 |
| 2015/0157512 | A1* | 6/2015 | Abir | A61B 5/08 340/573.5 |
| 2016/0125759 | A1* | 5/2016 | Dougherty | G09B 19/00 434/236 |

FOREIGN PATENT DOCUMENTS

| | | |
|---|---|---|
| WO | 9933037 A1 | 7/1999 |
| WO | 02052302 A2 | 7/2002 |

OTHER PUBLICATIONS

ISR_WO 12072018, International Search Report and Written Opinion cited in corresponding International PCT App No. PCT/CA2018/051164; dated Dec. 7, 2018; 8 pp.

* cited by examiner

300

| Events All Tag Managers + | | |
|---|---|---|
| Tag Name | Name: | Tag 1 |
| Tag 0  T: 72.4°F  ▫▫▫<br>H:30%; 51s ago | Temperature: | 35°C/96°F > |
| Tag 1  T: 95.5°F  ▫▫▫<br>H:32%;  7s ago | Humidity: | 32%/61°F > |
| | Motion Sensor: | Disarmed > |
| | Updated: | 7 seconds ago > |
| | Battery: | 3.03 volts, 92% left > |
| | Signal: | -87 dBm (6% power) > |
| | Beep Options: | 5 times > |

FIG. 8D

INCONTINENCE CARE SYSTEM AND METHOD THEREFOR

CROSS-REFERENCE TO RELATED APPLICATIONS

This application is a U.S. National Stage of and claims priority benefit to prior filed International Application No. PCT/CA2018/051164, filed Sep. 18, 2018, and which claims the benefit of priority to U.S. Provisional Patent Application Ser. No. 62/560,390 filed Sep. 19, 2017, the content of which are incorporated herein by reference in their entirety.

FIELD OF THE DISCLOSURE

The present disclosure relates generally to personal care systems and methods, and in particular to an incontinence care system for detecting voiding events of a care-receiver and a method therefor.

BACKGROUND

People with disabilities, impairments and/or special needs (collectively denoted as care-receivers hereinafter) often face serious personal care difficulties. For example, people with impaired mobility generally rely on wheelchairs for a significant amount of time each day, and consequently, face hygienic issues as they often have to urinate or void into a diaper or briefs or clothing when they are in wheelchairs. Sitting in urine-soaked briefs for prolonged period of time causes health issues such as urinary tract infections (UTI), various skin ailments, and the like. Many professionals and organizations provide a wide variety of suggestions for dealing with such issues. For example, Everyday Health (www.everydayhealth.com) provides articles regarding skin rashes and overactive bladder with advices to avoid developing skin rashes.

The occurrence of voiding events is generally unpredictable even if highly scheduled meals are provided to the care-receivers. Caregivers may help care-receivers with incontinence care by regularly changing their protective undergarments such as briefs and underwear. However, caregivers often do so under their own schedules rather than at the care-receivers' needs, at least partially because it is generally difficult to promptly determine when a change of soiled undergarments is required. Consequently, the care-receivers may have to spend significant amounts of time in soiled incontinence undergarments, thereby putting them at risk for UTIs and other diseases resulting increased medical care and cost, and in the worst cases, may result in severe UTI complications and death.

Voiding event detection using disposable sensor units integrated directly into disposable underwear is known. For example, the SIM™ sensor offered by Simavita Limited of North Sydney, Australia, is a single-use disposable device built into a disposable brief to measure, record, and wireless transmit voiding events to a server for creation of a profile to be used for a patient's care. However, such single-use sensors are cost-ineffective and are not environmentally friendly.

Voiding event detection using removable sensors that connect to the disposable undergarment is also known. For example, talli offered by Sensassure of Toronto, ON, Canada, is a sensor device in a form of a reusable strip attachable to the outside of a diaper or brief for detecting voiding events using a non-contact moisture-sensing method. However, such removable sensors have the risk of being soiled and present sanitation concerns due to their placement. Generally, such sensors have to be removed, cleaned, disinfected, and reattached each time when a brief is changed, thereby causing increased amounts of time required by caregivers during providing requisite care.

SUMMARY

According to one aspect of this disclosure, there is disclosed a method of detecting a voiding event of a care-receiver. The method comprises measuring temperatures in real-time at a location adjacent a lower portion of the care-receiver's torso where the voiding event is to occur; and determining the voiding event based on the measured temperatures.

In some embodiments, said determining the voiding event based on the measured temperatures comprises: determining the voiding event if the measured temperatures rises above an upper boundary of a predefined temperature range.

In some embodiments, said determining the voiding event based on the measured temperatures comprises: determining the voiding event if the measured temperatures rises above an upper boundary of a predefined temperature range at a variation rate greater than or equal to a temperature-rising rate-threshold.

In some embodiments, said determining the voiding event based on the measured temperatures comprises: determining the voiding event if the measured temperatures rise at a rate greater than or equal to a temperature-rising rate-threshold.

In some embodiments, the temperature-rising rate-threshold is about 0.5° F. per three minutes.

In some embodiments, the temperature-rising rate-threshold is about 0.5° F. per five minutes.

In some embodiments, said location is a location in a seat or a location in a bed.

In some embodiments, the method further comprises: generating an alarm signal if the voiding event is determined.

In some embodiments, the method further comprises: determining a change event if the measured temperatures drop at a rate greater than or equal to a temperature-drop rate-threshold.

In some embodiments, the method further comprises: determining a change event if the measured temperatures drop subsequent to the voiding event and at a rate greater than or equal to a temperature-drop rate-threshold.

In some embodiments, the temperature-drop rate-threshold is about 1° F. per 3 minutes.

In some embodiments, the method further comprises: determining a weight reduction; and determining a change event if the determined weight reduction is greater than or equal to a weight-drop threshold.

In some embodiments, the method further comprises: disabling the alarm signal after the change event is determined.

In some embodiments, the method further comprises: measuring a weight; and starting said measuring temperatures step if the weight measurement is greater than a weight threshold.

In some embodiments, the method further comprises at least one of: transmitting the measured temperatures to a remote computing device; and if the voiding event is determined, transmitting the determined voiding event to the remote computing device.

In some embodiments, the method further comprises: generating, on the remote computing device, an indication of the detected voiding event.

In some embodiments, the method further comprises: storing the measured temperatures.

In some embodiments, the method further comprises: measuring a humidity; and determining a leak event if the measured humidity is greater than or equal to a humidity threshold.

According to one aspect of this disclosure, there is disclosed an apparatus for detecting a voiding event of a care-receiver, The apparatus comprises: a heat-conductive component locatable at a location adjacent a lower portion of the care-receiver's torso where the voiding event is to occur; a temperature sensor module coupled to the heat-conductive component for measuring temperatures in real-time; a controlling circuitry coupled to the temperature sensor; and a power source for powering the temperature sensor module and the controlling circuitry. The controlling circuitry is configured for: receiving temperatures measured by the temperature sensor; and determining the voiding event based on the measured temperatures.

In some embodiments, said temperature sensor module comprises the heat-conductive component.

In some embodiments, said heat-conductive component is a heat-conductive strip or heat-conductive plate separated from and coupled to the temperature sensor module.

In some embodiments, said determining the voiding event based on the measured temperatures comprises: determining the voiding event if the measured temperatures rises above an upper boundary of a predefined temperature range.

In some embodiments, said determining the voiding event based on the measured temperatures comprises: determining the voiding event if the measured temperatures rises above an upper boundary of a predefined temperature range at a variation rate greater than or equal to a temperature-rising rate-threshold.

In some embodiments, said determining the voiding event based on the measured temperatures comprises: determining the voiding event if the measured temperatures rise at a rate greater than or equal to a temperature-rising rate-threshold.

In some embodiments, the temperature-rising rate-threshold is about 0.5° F. per three minutes.

In some embodiments, the temperature-rising rate-threshold is about 0.5° F. per five minutes.

In some embodiments, said location is a location in a seat or a location in a bed.

In some embodiments, the apparatus further comprises an alarm module; and the controlling circuitry is further configured for: generating an alarm signal if the voiding event is determined.

In some embodiments, the controlling circuitry is further configured for: determining a change event if the measured temperatures drop at a rate greater than or equal to a temperature-drop rate-threshold.

In some embodiments, the controlling circuitry is further configured for: determining a change event if the measured temperatures drop subsequent to the voiding event and at a rate greater than or equal to a temperature-drop rate-threshold.

In some embodiments, the temperature-drop rate-threshold is about 1° F. per 3 minutes.

In some embodiments, the apparatus further comprises a pressure sensor module; and the controlling circuitry is further configured for: determining a weight reduction using the pressure sensor module; and determining a change event if the determined weight reduction is greater than or equal to a weight-drop threshold.

In some embodiments, the apparatus further comprises a pressure sensor module; and the controlling circuitry is further configured for: measuring a weight using the pressure sensor module; and starting said measuring temperatures step if the weight measurement is greater than a weight threshold.

In some embodiments, the controlling circuitry is further configured for: disabling the alarm signal after the change event is determined.

In some embodiments, the apparatus further comprises a wireless communication module; and the controlling circuitry is further configured for using the wireless communication module for at least one of: transmitting the measured temperatures to a remote computing device; and if the voiding event is determined, transmitting the determined voiding event to the remote computing device.

In some embodiments, the apparatus further comprises a storage; and the controlling circuitry is further configured for: storing the measured temperatures in said storage.

In some embodiments, the apparatus further comprises a water-proof cover; and a heat-conductive strip coupled to the temperature sensor module and extending to a location of the cover for positioning adjacent the lower portion of the care-receiver's torso where the voiding event is to occur.

In some embodiments, the apparatus further comprises a humidity sensor module; and the controlling circuitry is further configured for: measuring a humidity; and determining a leak event if the measured humidity is greater than or equal to a humidity threshold.

According to one aspect of this disclosure, there is disclosed a system for detecting a voiding event of a care-receiver. The system comprises: a detection apparatus and a computing device coupling to the detection device via at least a wireless network. Said detection apparatus comprises: a heat-conductive component locatable at a location adjacent a lower portion of the care-receiver's torso where the voiding event is to occur, a temperature sensor module for measuring temperatures in real-time, a wireless communication module, a controlling circuitry coupled to the temperature sensor, and a power source for powering the temperature sensor module, the wireless communication module and the controlling circuitry. The controlling circuitry is configured for: receiving temperatures measured by the temperature sensor; and transmitting the measured temperatures to the computing device. The computing device is configured for: determining the voiding event based on the measured temperatures.

BRIEF DESCRIPTION OF THE DRAWINGS

FIGS. 8A to 8D show examples of a graphic user interface (GUI) displayed on a client computing device of the incontinence care system shown in FIG. 1;

DETAILED DESCRIPTION

Figure 1:
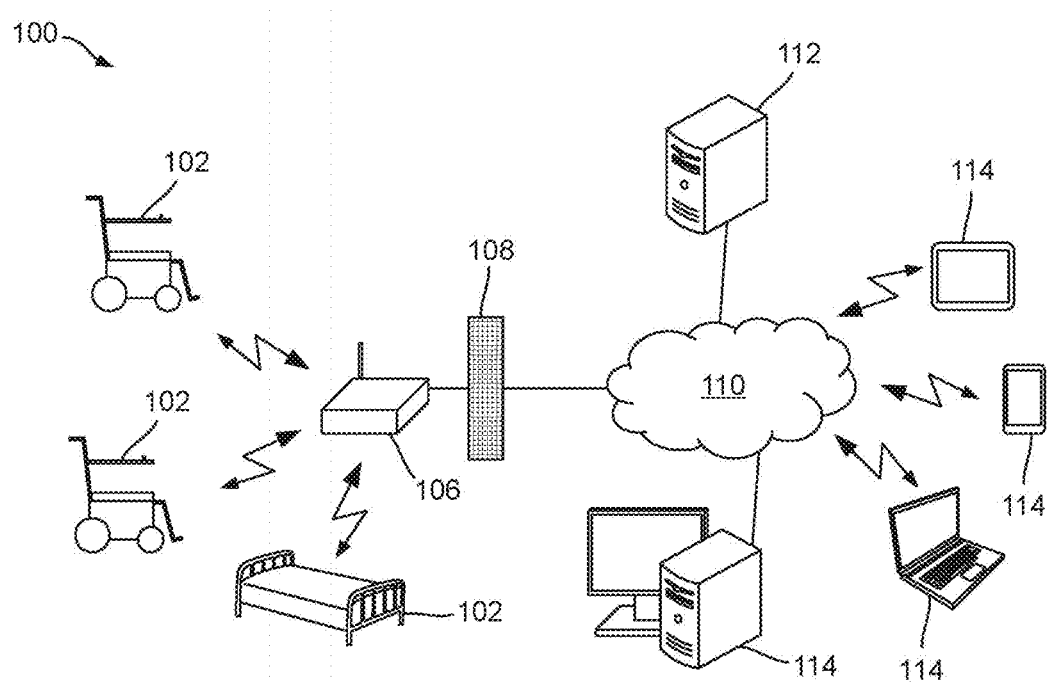
FIG. 1 is a schematic diagram showing an incontinence care system according to some embodiments of this disclosure.

Embodiments herein disclose an incontinence care system having one or more assistive devices for care-receivers. Each assistive device comprises an incontinence care apparatus coupled to a seating area. For example, an incontinence care apparatus may be integrated into a thin, flexible pad that may be attached to or alternatively, embedded into a wheelchair seat cushion. Alternatively, the incontinence care apparatus may be placed onto a mattress underneath a bedding sheet. The incontinence care apparatus comprises one or more sensor modules for measuring changes in selected environmental parameters, for example temperature and/or humidity, and for sending alerts to caregivers when the magnitudes of the measured changes signal that personal care is required for a care-receiver.

The incontinence care apparatus of the assistive device provides accurate and timely detection of voiding events, and timely communicates detected voiding events to caregivers via suitable means such as audible alarm signals.

The incontinence care apparatus of the assistive device also allows resetting the condition of a voiding event, and has a small form factor and a high energy efficiency.

In some embodiments, the incontinence care apparatus comprises at least a temperature sensor module positioned on or about a seating area of the assistive device for collecting at least the temperature data thereon. The system identifies temperature variation patterns from the collected temperature data, and determines the occurrence of voiding events based on variations in the measured temperature data in reference to the identified temperature variation patterns.

In some embodiments, the system calculates a variation rate of the collected temperature data, and uses the variation rate to determine the occurrence of voiding events. In some embodiments, a baseline temperature range is determined, and a voiding event is determined if the measured temperature rises above an upper boundary of the baseline temperature range at a variation rate greater than or equal to a selected threshold rate.

In some embodiments, one or more incontinence care apparatuses may additionally comprise one or more humidity sensors for detection of fluctuations in moisture about the sensors. In some embodiments, one or more incontinence care apparatuses may additionally comprise one or more pressure sensor modules for detecting change events (that is, events during which a care- receiver is removed from the assistive device by a caregiver for changing their protective undergarments).

In some embodiments, the system also comprises one or more server computers and one or more client computing devices. As is known in the art, the server computer and/or the client computing device may be a computing device comprising for example, a processing unit, memory including system memory (volatile and/or non-volatile memory) and/or other non-removable or removable memory (e.g., a hard disk drive, RAM, ROM, EEPROM, CD-ROM, DVD, solid-state memory, flash memory, etc.), a networking interface (e.g., using Ethernet, WiFi, and/or other suitable network format, to enable connection to shared or remote drives, one or more networked computers, or other networked devices), input/output components (e.g., keyboard, mouse, touchscreen, monitor, and/or the like), and a system bus coupling the various computer components to the processing unit. The server computer and/or the client computing device executes computer-readable code or instructions stored on the memory for performing various actions.

The incontinence care apparatuses may transmit collected temperature data to the server computers via wireless connections such as BLUETOOTH® (BLUETOOTH is a registered trademark of Bluetooth Sig. Inc., Kirkland, WA, USA) and/or WI-FI® (WI-FI is a registered trademark of Wi-Fi Alliance, Austin, Tex., USA). The server computers may process the received temperature data to detect the occurrence of voiding events and if voiding events are detected, send voiding event notifications to the client computing devices.

In some embodiments, the incontinence care apparatuses may comprise a dual BLUETOOTH®/WI-FI® radio communication means for scalable uses such as from home use by family caregivers to large-scale use in institutional facilities.

Turning now to FIG. 1, shown is an example of an incontinence care system generally identified using reference numeral 100. The incontinence care system 100 comprises one or more assistive devices 102 such as, motorized wheelchairs, un-motorized wheelchairs, beds, and the like, for use by care-receivers. Each assistive device 102 comprises an incontinence care apparatus 204 (see FIG. 3) for voiding-event detection and for wireless communication with a managing device 106 such as a manager device for managing the incontinence care apparatuses, a wireless router, a network switch, a gateway, a wireless access point, and the like, via suitable wireless communication means such as WI-FI®, BLUETOOTH®, ZIGBEE® (ZIGBEE is a registered trademark of ZigBee Alliance Corp., San Ramon, Calif., USA), Z-WAVE® (Z-WAVE is a registered trademark of Silicon Laboratories Inc. of Austin, Tex., USA) 3G and 4G wireless mobile telecommunications technologies, a proprietary wireless communication technology, and/or the like. For example, in these embodiments, the incontinence care apparatus 204 may use BLUETOOTH® for wireless communication with the managing device 106.

The managing device 106 is in turn connected to a network 110 such as the Internet through a firewall 108. The connections between the managing device 106 and the firewall 108, and between the firewall 108 and the network 110 may be any suitable wired or wireless communication means such as Ethernet, USB cables, serial communication cables, parallel communication cables, WI-FI®, BLUETOOTH®, ZIGBEE®, Z-WAVE®, 3G and 4G wireless mobile telecommunications technologies, and/or the like.

The system 100 also comprises one or more server computers 112 connected to the network 110 for communication with the managing device 106 via the network 110 and through the firewall 108 to receive voiding event data and optionally, other data about the assistive devices 102 and the incontinence care apparatuses 204 thereof. The one or more server computers 112 may also manage the assistive devices 102 via the managing device 106.

The system 100 may further comprise one or more client computing devices 114 such as desktop computers, laptop computers, tablets, smartphones, Personal Digital Assistants (PDAs), and the like, connected to the network 110 for receiving voiding event notifications and related data. The users of the client computing devices 114 may be caregivers responsible for taking care of respective care-receiver(s). When a caregiver, being the user of a client computing device 114, receives a voiding event notification, the caregiver may then assist the care-receiver in a timely manner for a change. Thus, by using the system 100, caregivers may provide more personalized, efficient, and cost-effective care to care-receivers for dealing with voiding events.

In these embodiments, the users of the client computing devices 114 may also initiate commands for other tasks such as managing the assistive devices 102, reviewing historical voiding event data, conducting voiding event analysis, and the like.

Figure 2:
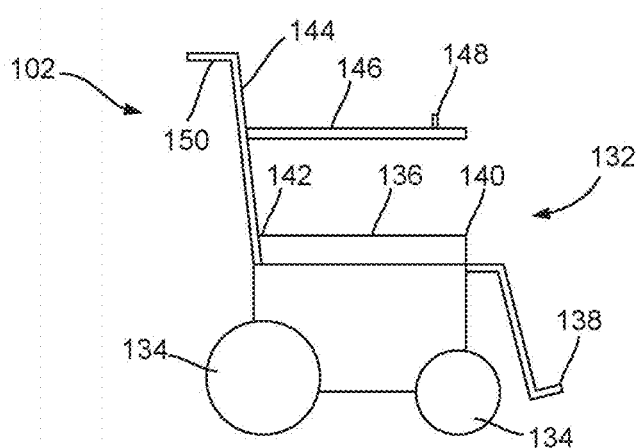
FIG. 2 is a schematic side-view of an assistive device of the incontinence care system shown in FIG. 1.

FIG. 2 shows an assistive device 102 in the form of a motorized wheelchair. As shown, the assistive device 102 comprises a seat 132 and a framework having four wheels 134. A motor (not shown) is installed in the seat 132 for driving the wheels 134.

The assistive device 102 may also comprise a seat cushion 136 installed or otherwise coupled onto the seat 132 for seating thereon of a care-receiver, a footrest 138 extending downwardly from a front end 140 of the seat 132 for foot-resting, a backrest 144 extending upwardly from a rear end 142 of the seat 132 for supporting the back of the care-receiver, and a pair of armrests 146 extending upwardly from two opposite sides of the seat 132. One of the armrests 146 such as the armrest on the right-hand side may comprise a steering handle 148 for wheelchair driving control. The backrest 144 comprises a pair of push handles 150 rearwardly extending from a top end thereof for a caregiver to manually move the wheelchair 102.

Figure 3:
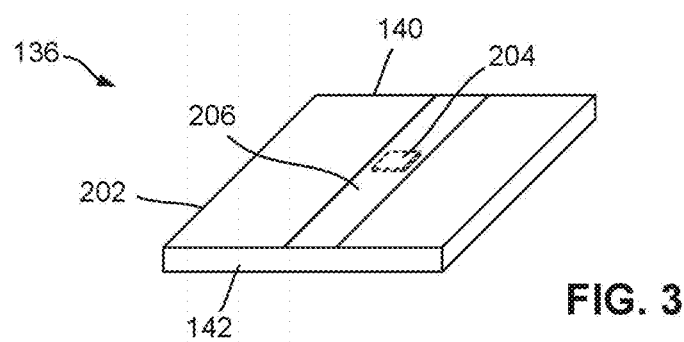
FIG. 3 show a seat cushion of the assistive device shown in FIG. 2, wherein the seat cushion comprises an incontinence care apparatus.

As shown in FIG. 3, the seat cushion 136 in these embodiments comprises a cushion block 202 made of a soft and/or flexible material such as foam and the like, an incontinence care apparatus 204 embedded in the cushion block 202 for detecting voiding events, and a heat-conductive component 206 in the form of a heat-conductive strip attached to a top surface of the cushion block 202 and extending from a front end 140 (corresponding to the front end 140 of the seat 132) to a rear end 142 (corresponding to the rear end 142 of the seat 132) and laterally about the central of the cushion block 202. The seat cushion 132 may also comprise a water-proof cover (not shown) for receiving therein the cushion block 202, the incontinence care apparatus 204 and the heat-conductive strip 206. The water-proof cover may comprise a hook and loop fastener, such as a VELCRO® flap (VELCRO is a registered trademark of Velcro Industries B.V., Curacao, Curacao), for easy access to the content therein.

The heat-conductive strip 206 is coupled to the incontinence care apparatus 204 for facilitating the temperature measurement and is positioned on the cushion block 202 at a location such that, when a care-receiver is accommodated in the assistive device 102, the heat-conductive strip 206 is at a location adjacent a lower portion of the care-receiver's torso where a voiding event is to occur. Such a position may be in a selected area of a surface upon which the care-receiver is sitting or reclining or laying.

In some embodiments, the heat-conductive strip 206 is sealed onto an outer surface of the water-proof cover and in heat-conductive contact (e.g., direct contact or via a metal component penetrating the water-proof cover) with the incontinence care apparatus 204. In some other embodiments, the heat-conductive strip 206 is received in the water-proof cover and in heat-conductive contact with the incontinence care apparatus 204.

Figure 4:
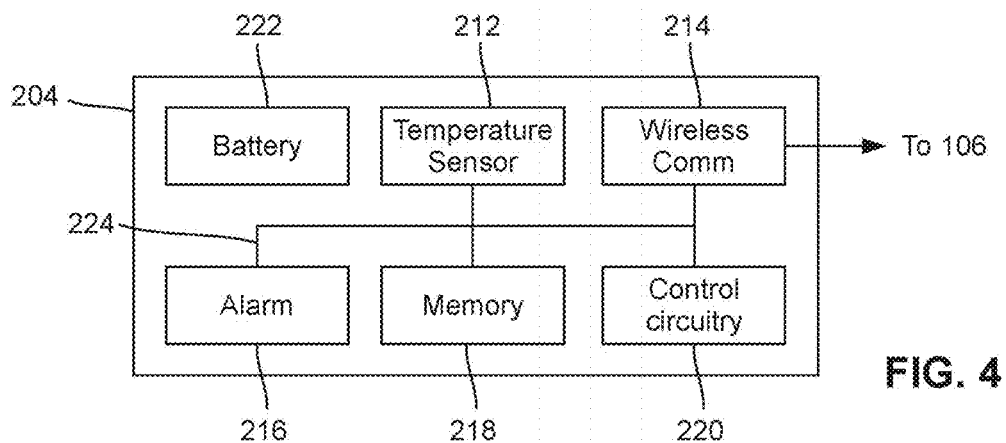
FIG. 4 is a schematic diagram showing the functional structure of the incontinence care apparatus shown in FIG. 3.

As shown in FIG. 4, the incontinence care apparatus 204 comprises a temperature sensor module 212, a wireless communication module 214, an alarm module 216, a memory 218, and a control circuitry 220 interconnected via one or more system buses 224 or other suitable circuitry. A replaceable battery 222 powers all modules of the incontinence care apparatus 204.

In these embodiments, the temperature sensor module 212 is functionally coupled to the heat-conductive strip 206 to collect temperature measurements in an extended range to enable reliable detection of voiding events. The temperature sensor module 212 may be any sensor or sensor module suitable for measuring temperature such as a thermistor, a thermocouple, a digital thermometer, or the like. Preferably, the temperature sensor module 212 has low energy consumption, small areal footprint, and low cost. The temperature sensor module 212 may also preferably require few ancillary components for reducing the complexity of the circuitry. In some embodiments, the temperature sensor may operate between 15° C. and 40° C. with a temperature measurement resolution of 0.01° C. or smaller, and a measurement time resolution of 30 seconds or smaller (i.e., one temperature measurement every 30 seconds or faster). In embodiments where the temperature sensor has a digital output or an analog-to-digital converter (ADC) is used for converting the analog output of the temperature sensor to digital, the digital output has a length of at least N-bit where $$N = \lceil \log_2(100 T_{range}) \rceil$$

with $T_{range}$ being the temperature measurement range of the temperature sensor, and $\lceil x \rceil$ representing the smallest integer greater than or equal to x. For example, in embodiments where $T_{range}$ is 1, 10, or 100, the digital output has a length of at least 7, 10, or 14 bits, respectively.

The wireless communication module 214 transmits collected temperature data to a receiving device which in these embodiments, is the managing device 106. The wireless communication module 214 may use any suitable wireless communication technology such as WI-FI®, BLUETOOTH®, ZIGBEE®, Z-WAVE®, 3G or 4G or 5G wireless mobile telecommunications technologies, a proprietary wireless communication technology, and/or the like. In various embodiments, the wireless communication technology used in the system 100 may be selected by a system designer based on the evaluation of the scalability, ubiquity, data rate, and range thereof.

For example, in some embodiments, the wireless communication technology may need to have a good scalability adaptable from connecting a dozen of incontinence care apparatuses 204 to connecting hundreds of incontinence care apparatuses 204 with a minimized cost increase. In some embodiments, the wireless communication technology may need to be a technology with global adoption and support.

While in some embodiments, the incontinence care apparatuses 204 may only infrequently transmit a small amount of voiding event data, in some other embodiments, the incontinence care apparatuses 204 need to frequently transmit a large amount of voiding event data and/or other data, and may require the wireless communication technology used in the incontinence care apparatus 204 to provide a sufficient data rate.

In different embodiments, the system 100 may have different requirements with respect to the range of the wireless communication technology. For example, in embodiments where the assistive devices 102 may be distributed in a large site such as a large building may require a wireless communication technology with a sufficiently large coverage.

The wireless communication technology is generally required to have a low power consumption such that the battery 222 of the incontinence care apparatus 204 does not need to be frequently changed or recharged. Moreover, the wireless communication technology is also generally required to have a low cost.

The alarm module 216 is an acoustic buzzer which generates an audible alarming signal for notifying the nearby caregiver that a voiding event has occurred. The memory 218 is a non-volatile memory such as a solid-state memory. Of course, those skilled in the art will appreciate that in various embodiments, the memory 218 may be other volatile and/or non-volatile memory such as RAM, ROM, EEPROM, flash drive, hard drives, or the like, with suitable supporting circuitry. The memory 218 is used for storing collected sensor data (such as temperature data) and other data generated during operation.

The control circuitry 220 controls the various components 212 to 218 during operation. In some embodiments, the control circuitry 220 may be a microcontroller such as a STM32L4 series microcontroller manufactured by STMicroelectronics of Geneva, Switzerland. The microcontroller 220 may communicate with the wireless communication module 214 via a SPI bus (as part of the system bus 224). In embodiments where a humidity sensor is used (described later), the microcontroller 220 may communicate with the wireless communication module 214 via an Inter-Integrated Circuit (I2C, also denoted as I²C) bus (as part of the system bus 224). The microcontroller 220 may execute the mbed platform/operating system for managing various modules 212 to 222.

The battery 222 may be any suitable battery such as one or more alkaline battery cells, button battery cells such as CR2032 and/or CR2025 battery cells, Lithium-ion battery cells, Lithium-polymer battery cells, and/or the like. The battery 222 may be non-rechargeable or rechargeable, depending on the system design. In embodiments wherein a non-rechargeable battery is used, the battery 216 is generally preferable to have a long operation life such as to be replaced about once a year, thereby proving ease of use with reduced maintenance needs.

Thus, a system designer may selects the modules 212 to 222 of the incontinence care apparatus 204 from a wide range of options based on the system requirements. In these embodiments, the temperature sensor 212 and the wireless communication module 214 are integrated as a wireless tag device with a temperature sensor such as a CAO Gadgets Wireless Sensor Tag with Temperature Sensor offered by CAO Gadgets LLC of Irvine, Calif., USA. A printed circuit board (PCB) with suitable circuitry is used for mounting and connecting the wireless tag device with other modules 216 to 222.

The system 100 processes the temperature data obtained from each assistive device 102. The obtained temperature data generally varies over time. The system 100 identifies patterns of the temperature variations, and detects the occurrence of voiding events and/or other out-of-normal physiological events based on the identified temperature variation patterns.

As will be described in more detail below, when a voiding event is detected, the alarm module 216 generates an audible alarming signal to notify a nearby caregiver that a voiding event has occurred. A message signaling the occurrence of a voiding event is also sent to one or more client computing devices 114 for notification of the users thereof. In these embodiments, the event notification comprises an audible notification signal broadcast by a speaker of the client computing device 114 along with presentation of a visual signal such as a red flag or bar displayed on a GUI of the client computing device 114. The audible alarming signal broadcast from the assistive device 102 and the audible notification signal broadcast from the client computing device 114 may last for a predefined period of time and then, turned off.

A caregiver may then remove the care-receiver from the assistive device 102 to remove and replace a soiled undergarment, thereby triggering a change event (described later). When a change event is detected, the system 100 notifies the client computing device 114 to turn off the visual signal.

Those skilled in the art will appreciate that, although manually turning off the audible and visual void-event-notification signals is technically feasible and may be implemented in some alternative embodiments, it is generally not preferable as these manipulations may lead to the risk that a caregiver may manually turn-off the void-event-notification signals but not follow through with removal and replacement of the soiled undergarment, thereby leaving the care-receiver susceptible to hygienic risks as a consequence of prolonged contact with the soiled undergarment.

The temperature detected by the temperature sensor module 212 is generally at about the ambient temperature (such as the room temperature when the assistive device 102 is in a room), for example at about 75 Fahrenheit degrees (° F.)

if a care-receiver is not sitting thereon. When a care-receiver sits on the seat 132 of the assistive device 102, the temperature detected by the temperature sensor module 212 increases with a mathematical model as follows (without a voiding event):

$$T_{sensor} = T_{body} - (T_{body} - T_{initial})e^{-t/\tau}, \quad (1)$$

where $T_{sensor}$ is the temperature detected by the temperature sensor module 212, $T_{body}$ is the external body temperature, $T_{initial}$ is the initial temperature of the temperature sensor module 212, $\tau$ is an empirically derived time constant, and t is time in seconds.

Equation (1) models the rising temperature measurement of the temperature sensor module 212 when the care-receiver is initially seated in the assistive device 102. The parameters $T_{initial}$, $T_{body}$, and $\tau$ may be obtained from experimental data.

Figure 5:
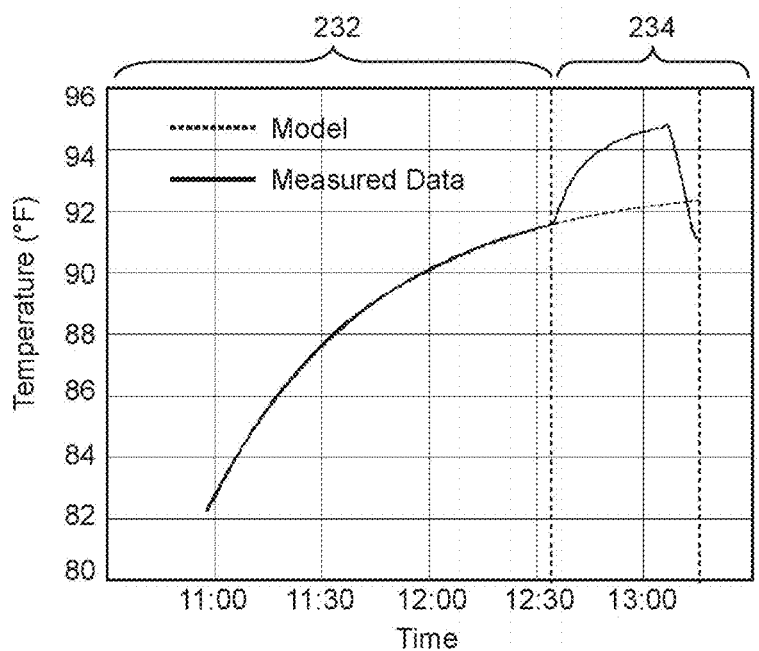
FIG. 5 shows a first temperature curve obtained using a temperature model and a second temperature curve representing the temperature data recorded by the incontinence care apparatus shown in FIG. 3 when the assistive device shown in FIG. 2 is used by a care-receiver.

FIG. 5 shows a plot of measured data of the temperature sensor module 212 (solid curve) and the temperature model of Equation (1) (dashed curve). In the "normal period" 232 when no voiding event occurs, the measured temperature data matches the temperature model of Equation (1) and gradually approaches a temperature upper boundary. On the other hand, in the "voiding period" 234 when a voiding event occurs, the measured temperature exhibits a significant increase and deviates from the model of Equation (1). Thus, a voiding event may be detected when the measured temperature deviates from the model of Equation (1).

Figure 6A:
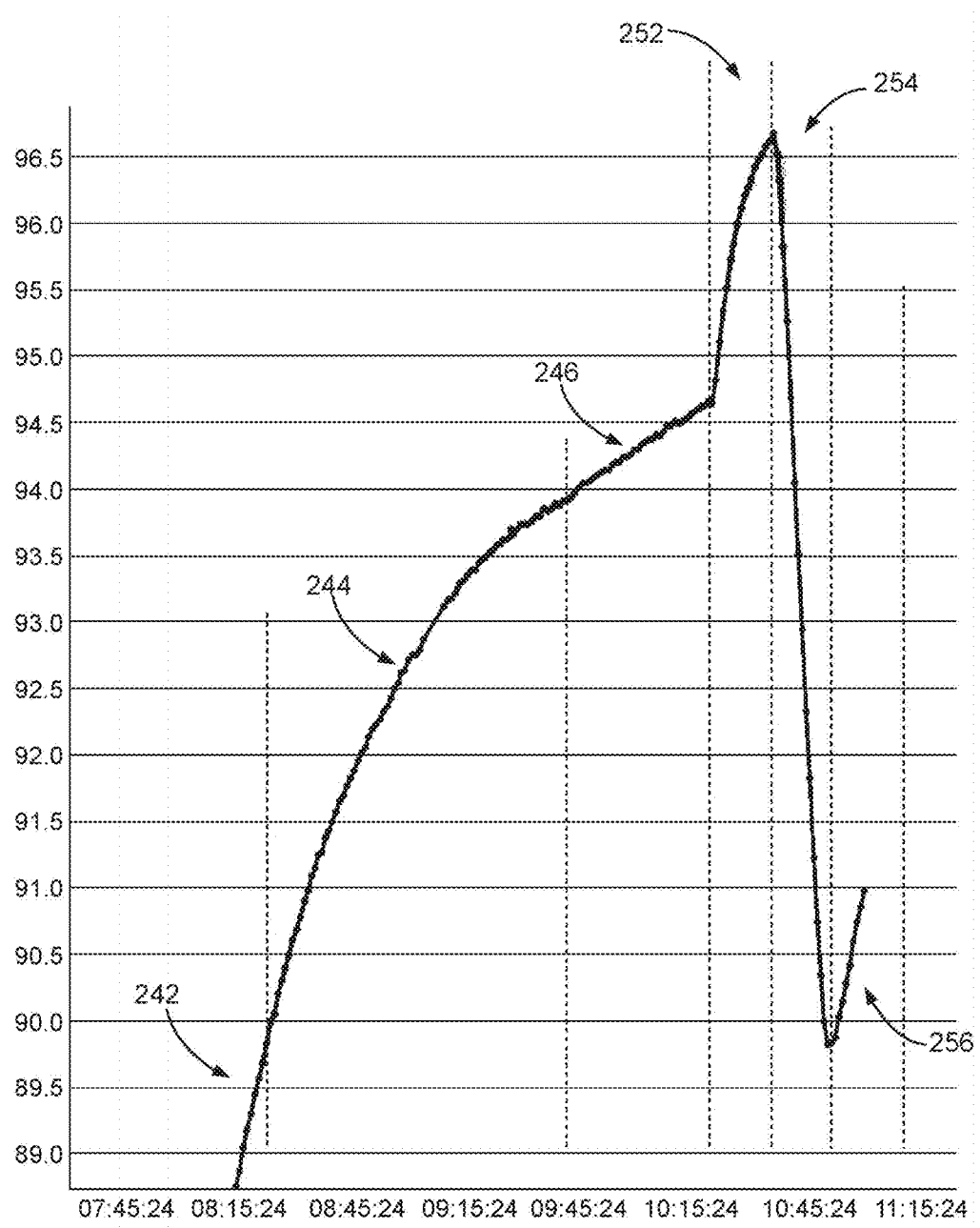
FIGS. 6A to 6C show temperature curves representing the temperature data recorded by the incontinence care apparatus shown in FIG. 3 when the assistive device shown in FIG. 2 is used by a care-receiver.

FIG. 6A shows a temperature curve representing the temperature data recorded by the incontinence care apparatus 204 when the assistive device 102 is used by a care-receiver.

As shown, the measured temperature rises at a slow rate over a period of about 30 minutes to the care-receiver's external body temperature for example, about 90° F. (see the curve section 242 shown in FIG. 6A). Then, the temperature detected by the temperature sensor module 212 may continue to increase at a slower rate to about 94° F. (curve section 244), and may further increase to about 95° F. at an even slower rate (curve section 246).

Therefore, a baseline temperature range may be defined for enabling detection of a voiding event. In these embodiments, the baseline temperature range may be a temperature range with a lower boundary of about 94.8° F. and an upper boundary of about 95.1° F., that is, between about 94.8° F. and about 95. ° F. In some alternative embodiments, the baseline temperature range may be between about 94° F. and about 95° F. In yet some alternative embodiments, the baseline temperature range may be between about 94.3° F. and about 95.3° F.

As indicated by the curve section 252 shown in FIG. 6A, when a voiding event occurs, the temperature detected by the temperature sensor module 212 exhibits a quick rise within a short period of time above the upper boundary of the baseline temperature range such as rising for about 0.5° F. to 1° F. or more above the upper boundary of the baseline temperature range (for example, to about 96.9° F.) within three (3) to ten (10) minutes.

After the voiding event has occurred, the care-receiver may be removed from the assistive device 102 for changing of the soiled undergarment. As indicated by the curve section 254 shown in FIG. 6A, the temperature detected by the temperature sensor module 212 exhibits a quick drop or reduction below the lower boundary of the baseline temperature range to about the ambient temperature within a short period of time. As indicated by the curve section 256, when the care-receiver is placed back onto the assistive device 102 after the change, the temperature detected by the temperature sensor module 212 again gradually rises to the baseline temperature range.

Figure 6B:
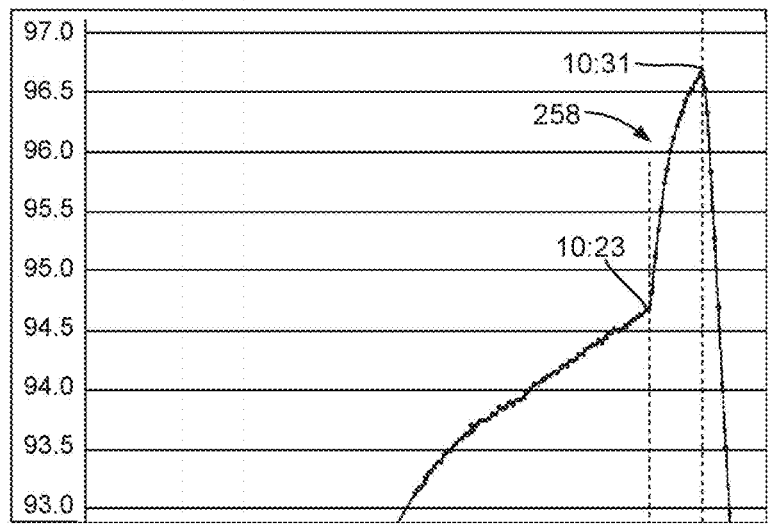

As shown in FIG. 6B, a voiding event occurs between 10:23 and 10:31 (curve section 258) during which the temperature quickly rises for about 2.1° F. from about 94.6° F. to about 96.7° F. within eight (8) minutes.

Figure 6C:
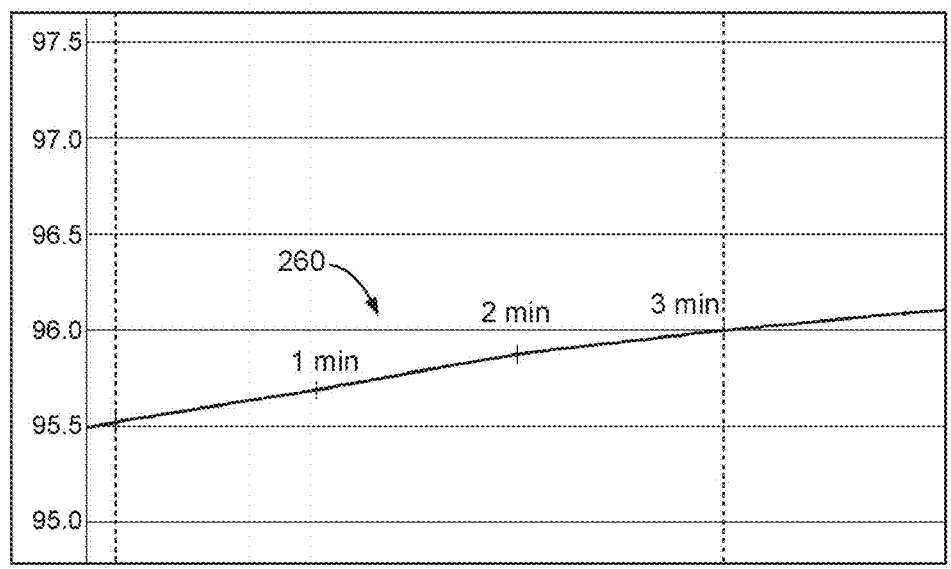

FIG. 6C shows another example. As shown, a voiding event occurs during which the temperature quickly rises for about 0.5° F. from about 95.5° F. to about 96.0° F. within 3 minutes (curve section 260).

Therefore, for each assistive device 102, the system 100 detects voiding events based on the temperature data collected in real time and its variation rate. In these embodiments, a voiding event is determined when the measured temperature rises from the upper boundary of the baseline temperature range at a rate greater than or equal to a threshold temperature rate. For example, the threshold temperature rate in these embodiments may be about 0.4° F. per 3 minutes (that is, temperature rising for at least about 0.4° F. within 3 minutes). In some alternative embodiments, a voiding event is determined when the temperature rises for at least about 0.5° F. above the upper boundary of the baseline temperature range within 3 minutes. In yet some alternative embodiments, a voiding event is determined when the temperature rises for at least about 0.5° F. above the upper boundary of the baseline temperature range within five (5) minutes.

Figure 7A:
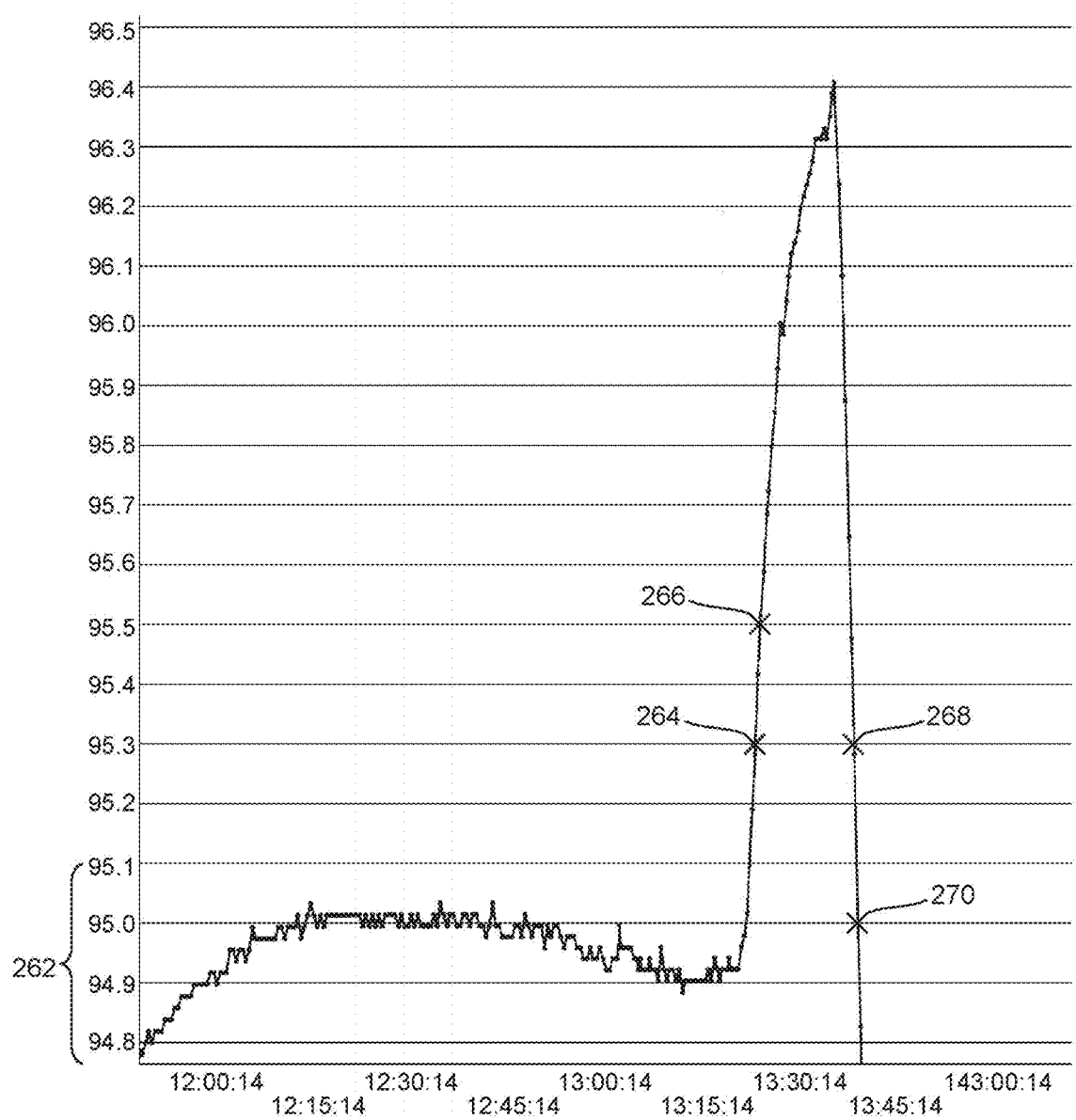
FIG. 7A shows a temperature curve representing the temperature data recorded by the incontinence care apparatus shown in FIG. 3 for detecting occurrence of voiding events.

FIG. 7A shows an example. In this example, a baseline temperature range 262 is set as between about 94.8° F. and about 95.1° F. A voiding event is determined and an audible alarming signal is generated when the temperature rises from the upper boundary (about 95.1° F.) of the baseline temperature range 262 to about 95.5° F. within 3 minutes (i.e., the temperature variation rate is at least about 0.4° F. per 3 minutes).

In the example shown in FIG. 7A, a caution notification such as an audible notification signal different than the audible alarming signal is first generated when the measured temperature rises from the upper boundary of the baseline temperature range 262 to a first temperature threshold 264 such as about 95.3° F. within a first time-period threshold such as about 2 minutes. In other words, the caution notification is generated when the measured temperature rises from the upper boundary of the baseline temperature range 262 to the first temperature threshold 264 with a temperature-rising rate greater than or equal to the first temperature-rate threshold.

When the temperature continues to rise to a second temperature threshold 266 such as about 95.5° F. within a second time-period threshold such as about 1 minute (i.e., rising from the upper boundary of the baseline temperature range 262 to the second temperature threshold 266 within about 3 minutes), an audible alarm signal is then generated. In other words, a voiding event is determined and the audible alarm signal is generated when the measured temperature rises from the upper boundary of the baseline temperature range 262 to the second temperature threshold 264 with a temperature-rising rate greater than or equal to the second temperature-rate threshold.

Those skilled in the art will appreciate that the threshold temperature rate may be generally denoted as $T = \Delta F/\Delta t$, where $\Delta t$ is a time range and $\Delta F$ is the temperature variation within the time range $\Delta t$. In various embodiments, $\Delta F$ and $\Delta t$ may be determined based on various factors such as the sampling rate and temperature resolution of the temperature sensor module 212. For example, in some embodiments, the temperature sensor module 212 has a sampling rate of one (1) sample per 30 seconds and a temperature resolution of 0.036° F. Therefore, the threshold temperature rate may be 0. ° F. per 30 seconds. In other words, a voiding event is determined and the audible alarming signal is generated when the temperature rises from the upper boundary of the baseline temperature range for at least 0.1° F. within 30 seconds.

In other words, the system applies a real-time moving window Δt to the measured temperature data, and checks if the temperature change within the moving window Δt is greater than or equal to a threshold value ΔF. In some embodiments, if the real-time temperature detected by the temperature sensor module 212 is greater than the upper boundary of the baseline temperature range 262 and the temperature change within the real-time moving window Δt is greater than or equal to the threshold value ΔF, a voiding event may be detected. As described above, the moving window Δt the threshold value ΔF may be determined based on various factors such as the sampling rate and temperature resolution of the temperature sensor module 212.

Figure 7B:
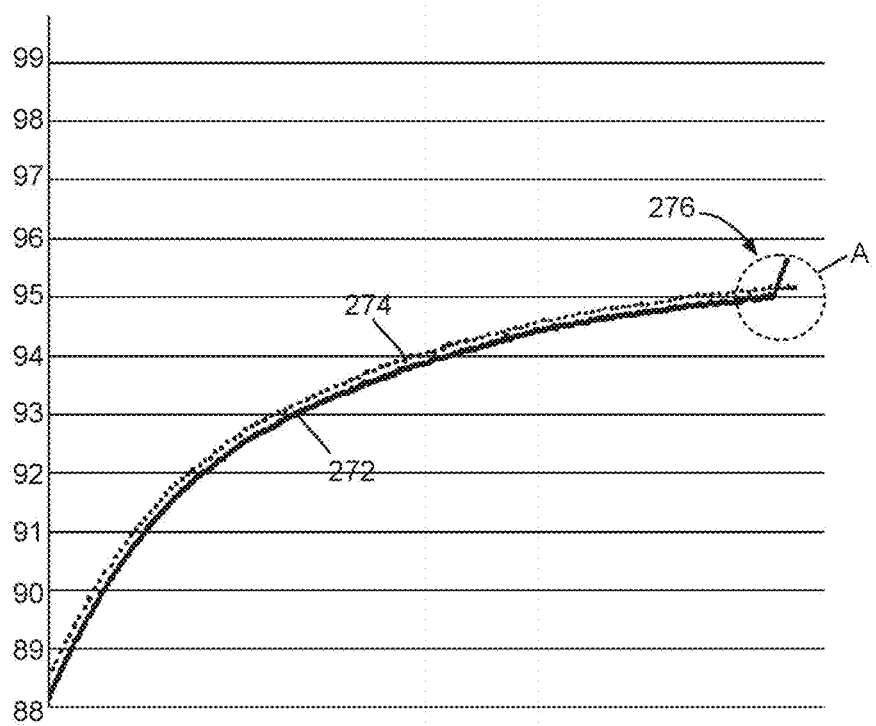
FIGS. 7B and 7C illustrate a temperature curve with the occurrence of a voiding event, and a temperature curve if a voiding event did not occur.
Figure 7C:
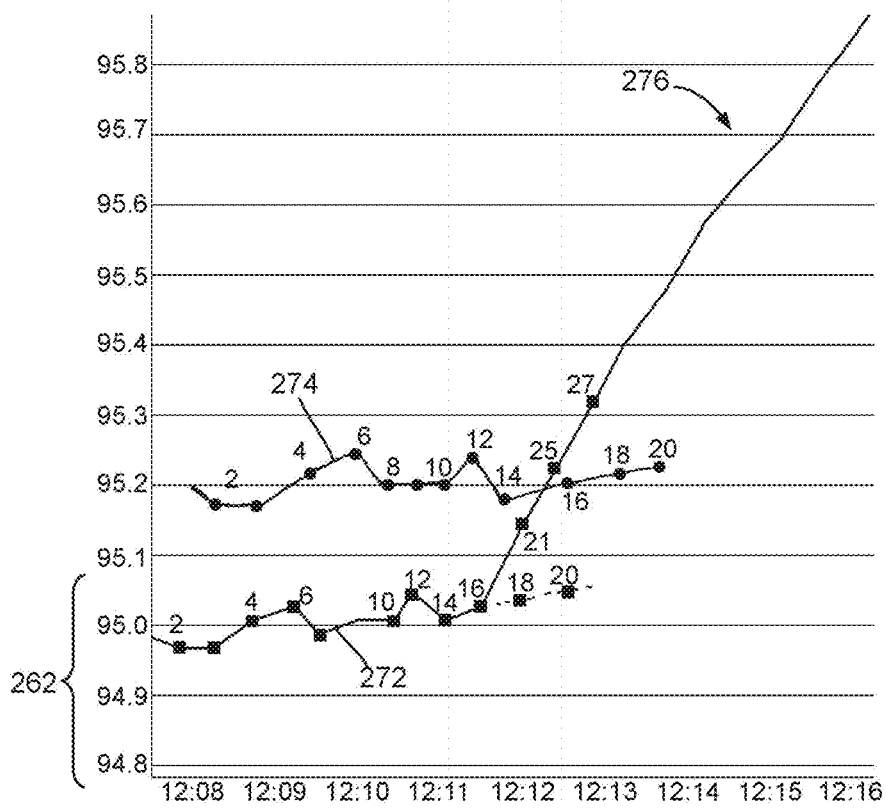

FIGS. 7B and 7C illustrate a temperature curve 272 with the occurrence of a voiding event 276, and as a comparison, a temperature curve 274 with no voiding event occurred. FIG. 7C is an enlarged illustration showing the area A of FIG. 7B. In both figures, the curve 274 is slightly shifted for illustrative purposes.

As shown, when no voiding event occurs, the temperature variation (shown on both curves 272 and 274) is smooth without any abrupt temperature changes. However, when a voiding event 276 occurs, the temperature (indicated by the curve 272) is abruptly and positively biased away from the curve during no voiding event occurred (indicated by the curve 274). As shown in FIGS. 7B and 7C, such an abrupt and positive temperature variation at a voiding event is a signal that can be quickly detected by the temperature sensor module 212 and is easily distinguishable from the "normal" temperature variation (i.e., the temperature variation when no voiding event occurs). Therefore, in some embodiments, the parameter Δt in the threshold temperature rate T may be a small time range such as a few seconds.

The system continues to monitor the temperature. As shown in FIG. 7A, a caution notification may be first generated when the measured temperature drops or reduces after the voiding event to a third temperature threshold 268 within a third time-period threshold. In other words, the caution notification is generated when the measured temperature drops after the voiding event to the third temperature threshold 268 with a temperature-rising rate greater than or equal to the third temperature-rate threshold.

A change event (i.e., an event during which the care-receiver receives a change) is determined when the temperature has dropped or reduced with a temperature-drop rate greater than or equal to a temperature-drop rate-threshold. For example, a change event may be determined when the temperature has dropped into the baseline temperature range such as to about 95° F. (see point 270 in FIG. 7A) within a short period of time such as within about 3 minutes (implying that the care-receiver is removed from the assistive device 102 for a change). In some embodiments, a change event is determined when the temperature drops for about 1° F. per 3 minutes. In some embodiments, a change event is determined only when a temperature drop occurred subsequent to a recently occurred voiding event and with a temperature-drop rate greater than or equal to the temperature-drop rate-threshold.

As described above, the wireless communication module 214 of the incontinence care apparatus 204 sends the collected temperature data to the managing device 106 which forwards the temperature data to the one or more server computers 112. The one or more server computers 112 process the received temperature data and generate event notifications and produce analytical results therefrom. The one or more server computers 112 then send the generated event notifications and analytical results to one or more client computing devices 114 for presentation to the users thereof via a GUI.

Figure 8A:
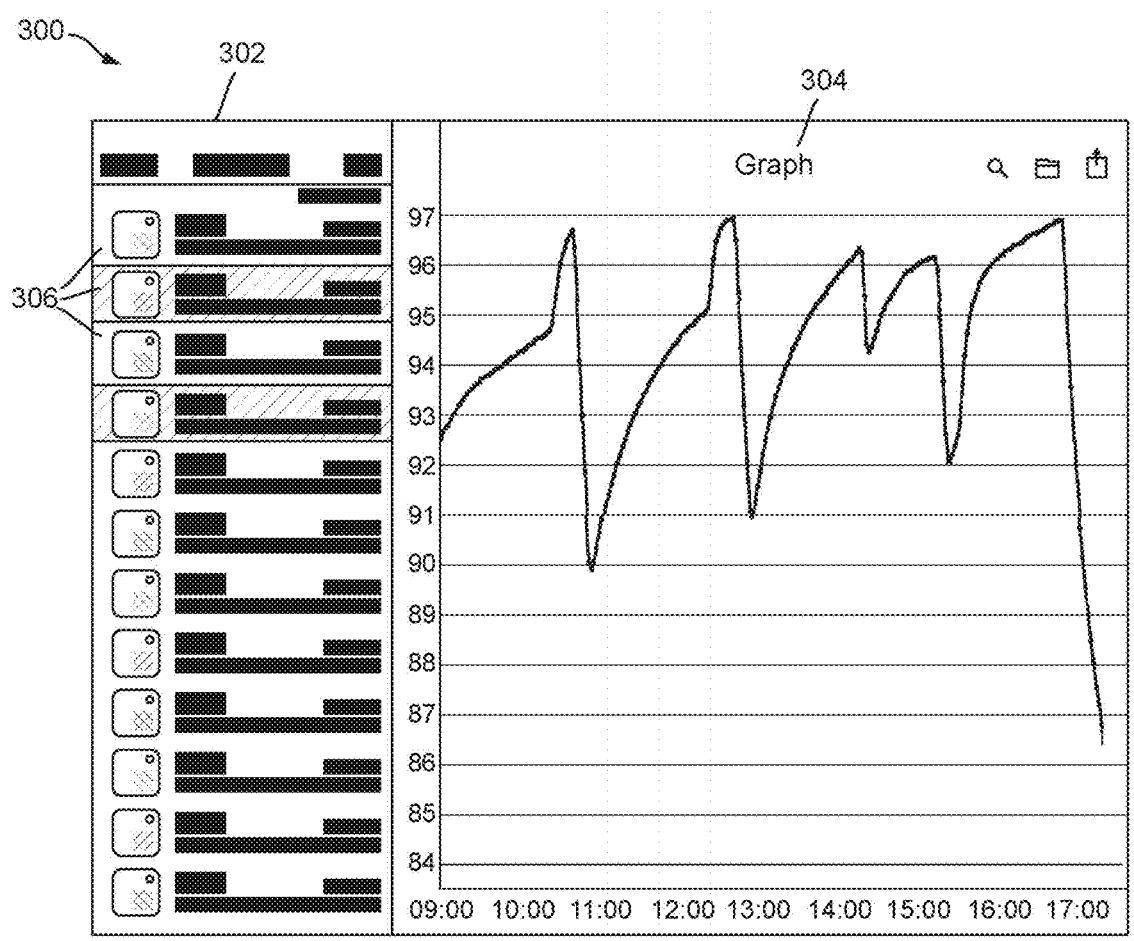

FIG. 8A shows an example of the GUI 300. As shown, the GUI 300 comprises an event notification area 302 and an analytical result area 304. The event notification area 302 lists the events 306 related to the system 100 such as user login, connection and disconnection of an incontinence care apparatus 204 of an assistive device 102, the occurrence of a voiding event, the occurrence of a change event, and/or the like, and the time instants that the events occurred. The analytical result area 304 shows analytical results such as a temperature curve with indication of occurred events, a table listing the collected temperature data with the collection time thereof, and/or the like.

Figure 8B:
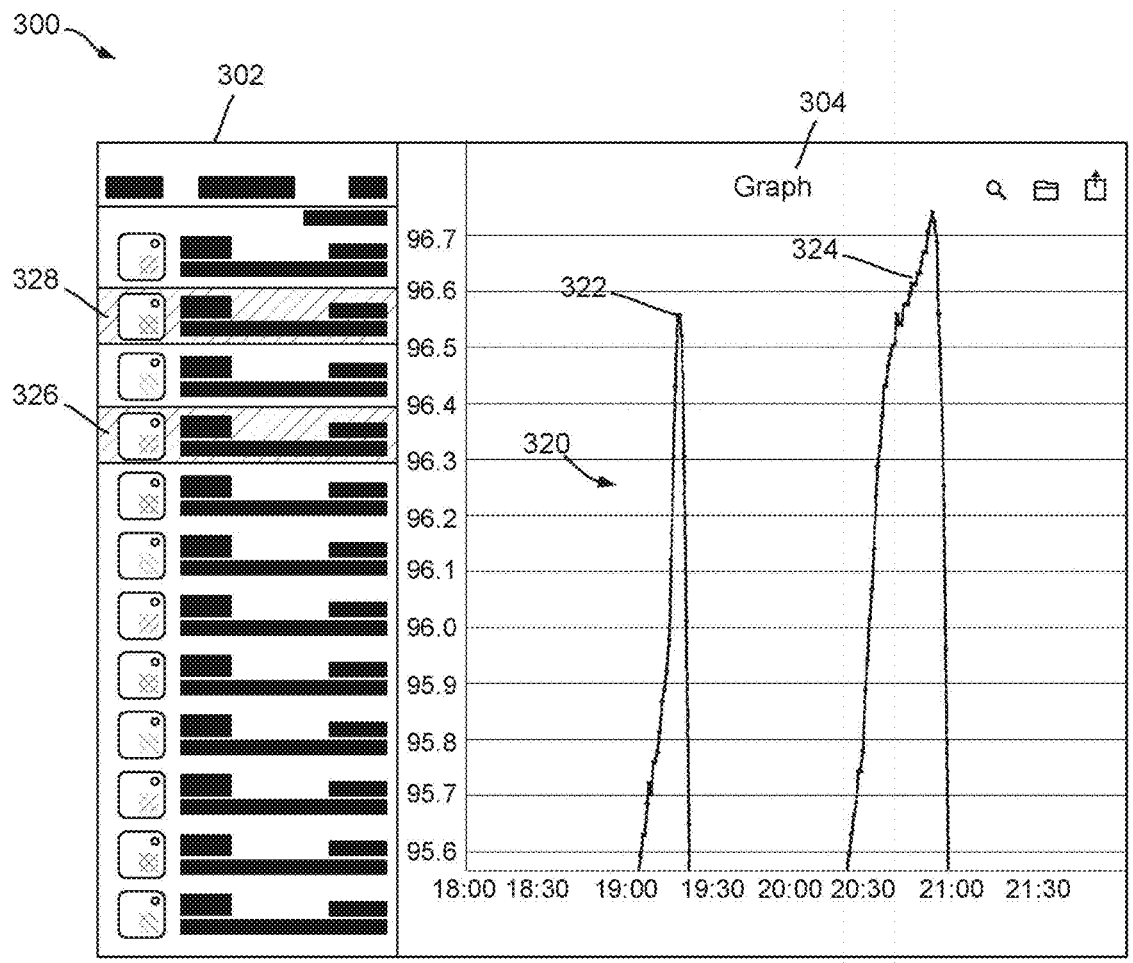

A user of the client computing device may manipulate the GUI 300 to view the events and analytical results. For example, the user may scroll up/down in the event notification area 302 to view recent and past events, and/or zoom in/out in the analytical result area 304 to view the temperature curve within a smaller/larger time range. FIG. 8B shows an example of the GUI 300 in which the user has zoomed in the temperature curve 320 to a small time range (May 26, 2017, from 18:00 to 21:30) to view the two temperature peaks 322 and 324 which correspond to the two events 326 and 328 shown in the event notification area 302, respectively.

Figure 8C:
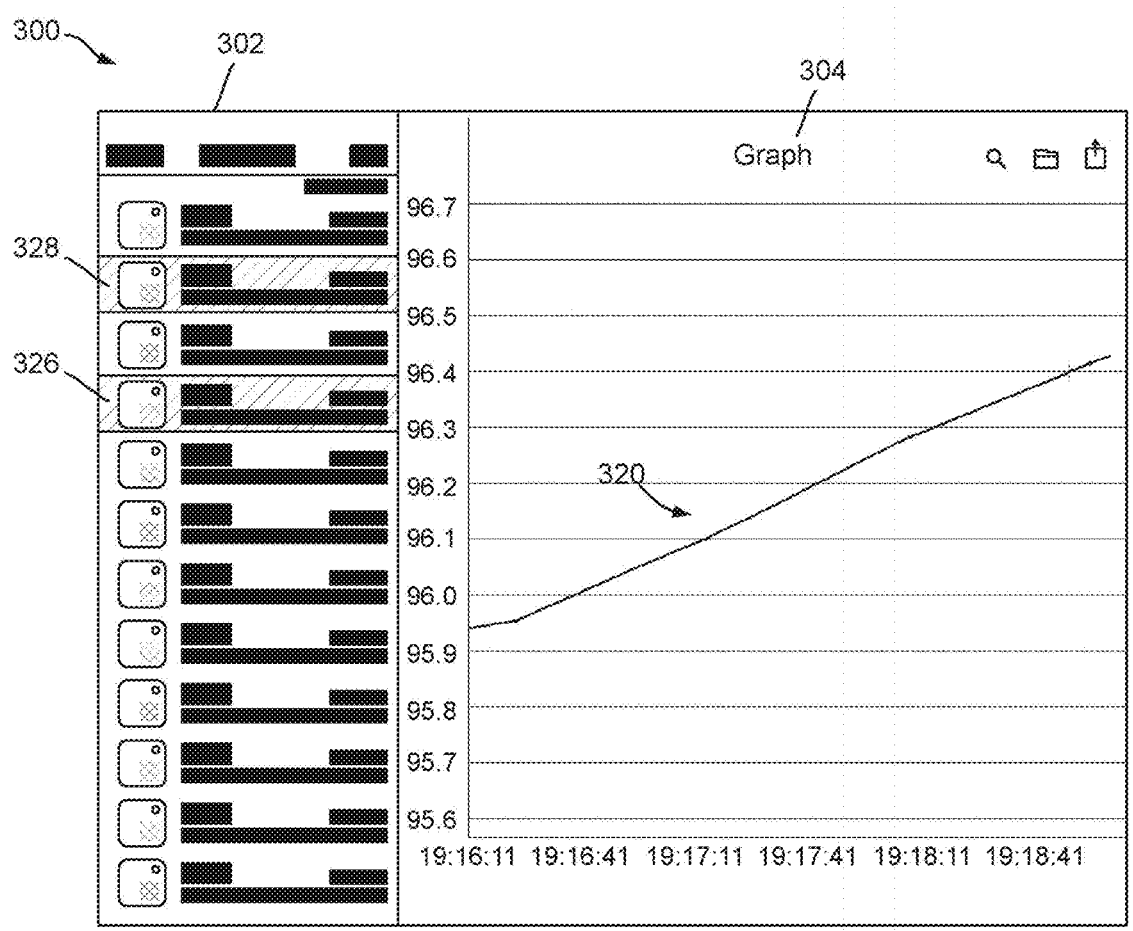

FIG. 8C shows an example of the GUI 300 in which the user has zoomed in the temperature curve 320 to a small time range (May 26, 2017, from 19:16 to 19:19). As shown, the temperature has increased for about 0.5° F. above the upper boundary of the baseline temperature range within 3 minutes, thereby triggering an alarm.

As shown in FIG. 8D, the GUI 300 may also display various system status and setting parameters such as the status and settings of the incontinence care apparatus 204.

FIG. 8D also shows that the GUI 300 may be used to show data and settings of a plurality of incontinence care apparatuses 204 (e.g., Tag0 and Tag1 shown in FIG. 8D).

In some situations, an assistive device 102 may be moved out of the communication range from the managing device 106. For example, a caregiver may move the care-receiver on a wheelchair 102 out of the house in which the managing device 106 is located. As the incontinence care apparatus 204 in these embodiments uses BLUETOOTH® for wirelessly communication with the managing device 106 and the BLUETOOTH® communication range is relatively small, the incontinence care apparatus 204 of an assistive device 102 may sometimes or even often lose wireless communication with the managing device 106 and consequently the one or more servers 102.

In these embodiments, the incontinence care apparatus 204 uses the alarm signal generated by the alarm module 216 thereof for reminding a caregiver to help the care-receiver in voiding events. Moreover, the incontinence care apparatus 204 stores temperature data collected from the temperature sensor module 212 in the memory 218. When the communication between the incontinence care apparatus 204 and the managing device 106 is re-established, the incontinence care apparatus 204 transmits the stored temperature data to the managing device 106 and deletes the transmitted temperature data from the memory to free the storage space.

Consequently, the real-time temperature curve shown in the GUI 300 may exhibit a gap when the communication between the incontinence care apparatus 204 and the managing device 106 is lost. Such a gap may be later filled with the temperature data received from the incontinence care apparatus 204 after the communication between the incontinence care apparatus 204 and the managing device 106 is re-established.

Figure 9:
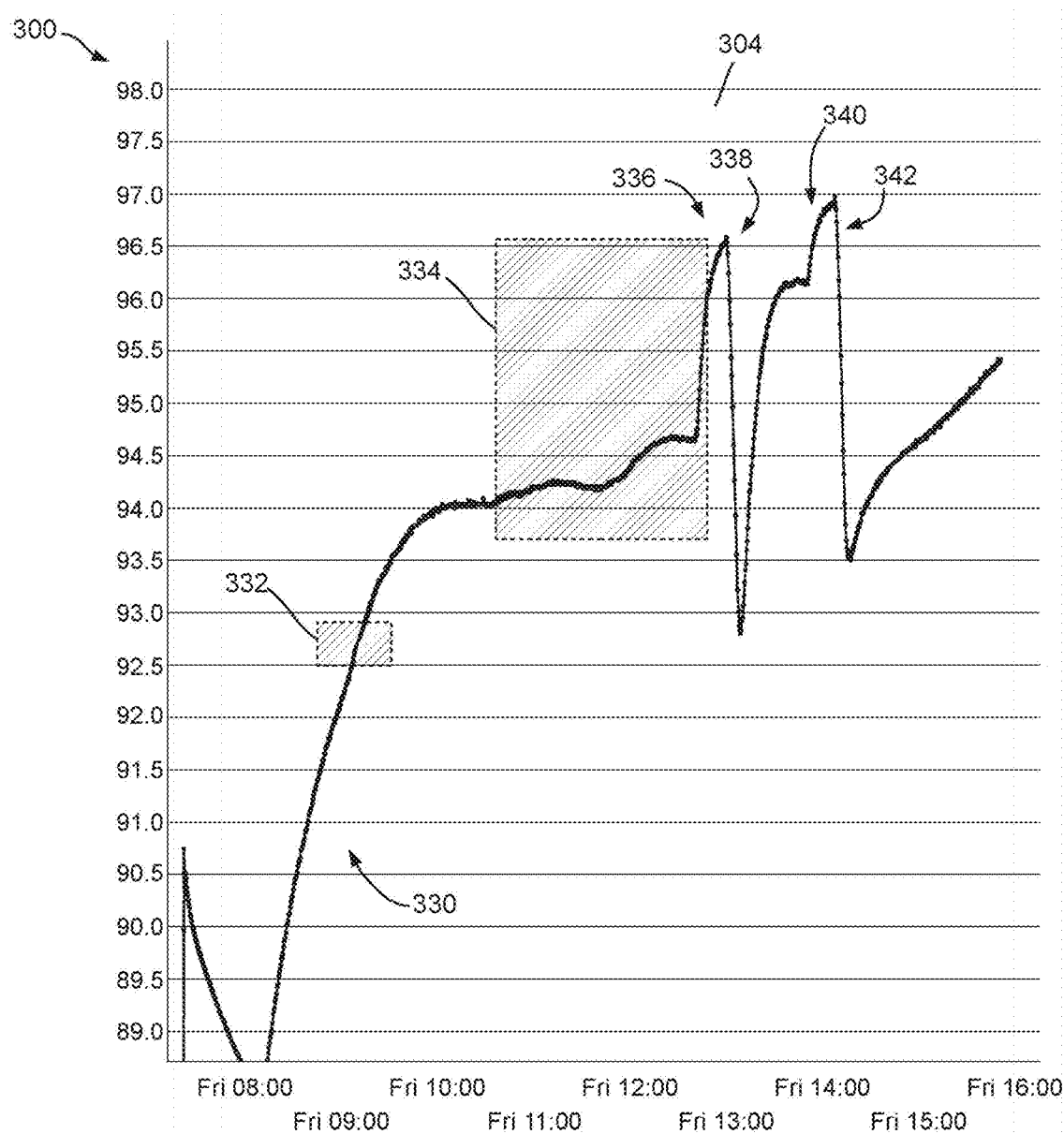
FIG. 9 shows a temperature curve representing the temperature data recorded by the incontinence care apparatus shown in FIG. 3 for detecting occurrence of voiding events when the assistive device shown in FIG. 2 is used by a care-receiver and is moved out of the communication range of a managing device of the incontinence care system shown in FIG. 1.

FIG. 9 shows an example. In this example, the care-receiver was on an assistive device 102 in the form of a wheelchair. The care-receiver initially stayed at home, and was later moved by the caregiver to a care facility. Then at later time, the caregiver moved the care-receiver to another location for a period of time, for example a treatment facility, and then returned the care-receiver back to the care facility. Managing devices 106 were only installed at the care-receiver's home and the care facility.

Therefore, the temperature curve 330 shown in the analytical result area 304 of the GUI 300 exhibits a plurality of sequential gaps. As shown in FIG. 9, a gap 332 was first shown from 9:15 AM to 9:21 AM when the care-receiver was on the way from home to the care facility and the BLUETOOTH® connection between the incontinence care apparatus 204 of the assistive device 102 and the managing devices 106 at home is lost.

After the care-receiver arrived at the care facility, the BLUETOOTH® communication between the incontinence care apparatus 204 and the managing device 106 at the care facility is established. Then, the temperature data stored in the incontinence care apparatus 204 is transmitted to the one or more server computers 112 via the managing device 106. The temperature curve 330 shown on the GUI 300 is then updated and the gap 332 is filled with temperature data collected between 9:15 AM and 9:21 AM (not shown).

Similarly, another gap 334 appeared in the period of time during which the care-receiver was moved out of the care facility to the treatment facility for a treatment and then returned to the care facility. A voiding event 336 was detected right before the care-receiver was moved back to the care facility, and the caregiver gave the care-receiver a change 338 after they were back to the care facility.

The BLUETOOTH® communication between the incontinence care apparatus 204 and the managing device 106 thereof was re-established and the stored temperature data was transmitted to the one or more server computers 112 after the care-receiver was back to the care facility. The updated curve 330 then shows the complete temperature curve 330 with a clear temperature variation pattern indicating the voiding event 336 occurred right before the care-receiver was returned to the care facility, and the corresponding change event 338. The temperature curve 330 also shows another voiding event and change event 340 and 342 that occurred during the stay at the care facility.

Those skilled in the art will appreciate that various alternative embodiments are readily available. For example, in some alternative embodiments, the baseline temperature range may be set at about 93° F. In other words, the upper and lower boundaries of the baseline temperature range are the same (about 93° F.) in these embodiments.

In some alternative embodiments, the baseline temperature range is periodically (such as daily) and automatically calibrated using a suitable machine learning method.

In above embodiments, the determination of a voiding event is based on both the baseline temperature range and the temperature variation rate. In some alternative embodiments, the determination of a voiding event may be based on the temperature values only. For example, a voiding event may be determined when the temperature value is above a threshold such as 95.5° F. In some alternative embodiments, the determination of a voiding event may be only based on the temperature variation rate T=ΔF/Δt. As described above, in various embodiments, ΔF and Δt may be determined based on various factors such as the sampling rate and temperature resolution of the temperature sensor module 212.

Figure 10A:
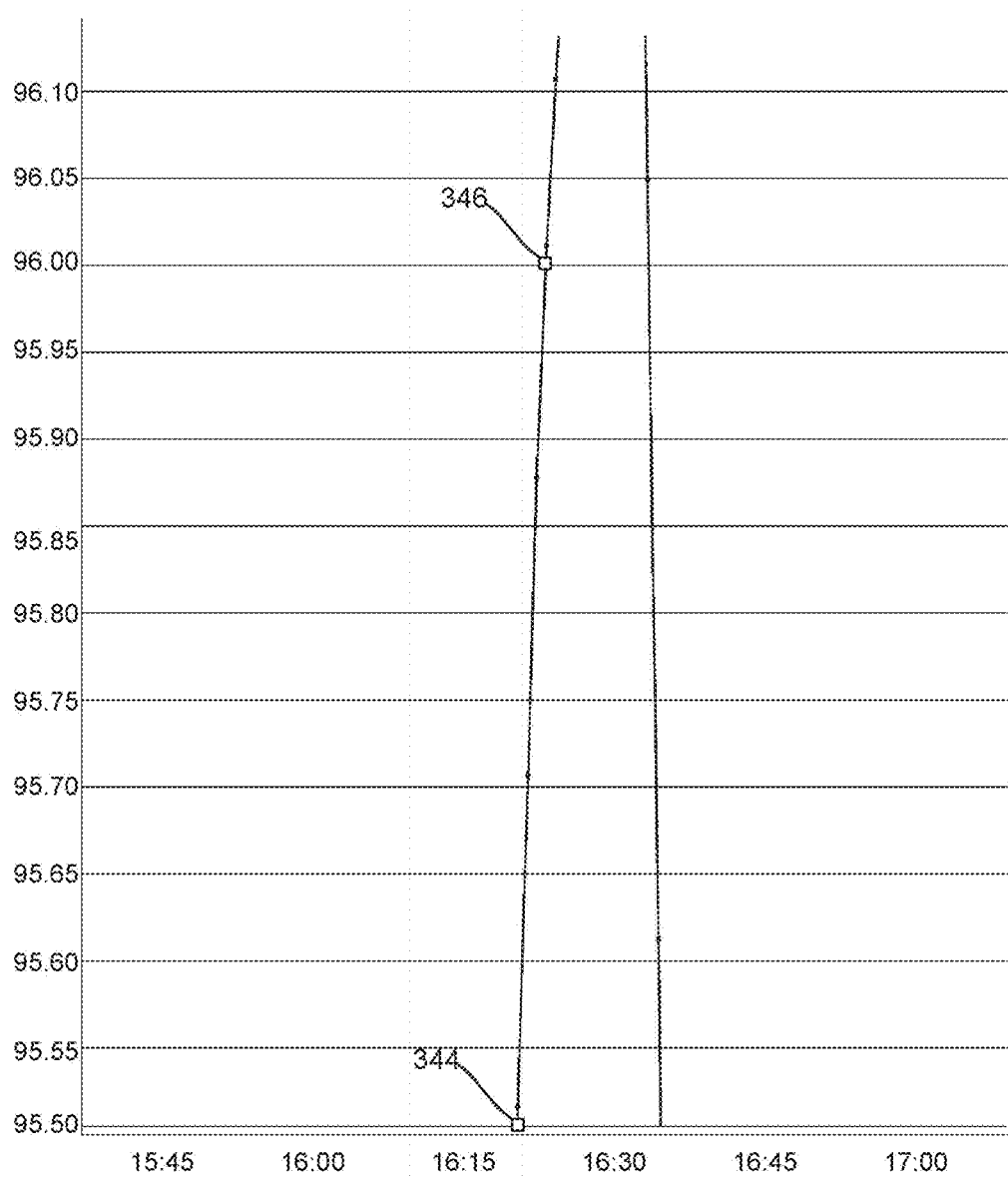
FIG. 10A shows a temperature curve representing the temperature data recorded by the incontinence care apparatus shown in FIG. 3 for detecting occurrence of voiding events, according to some alternative embodiments.
Figure 10B:
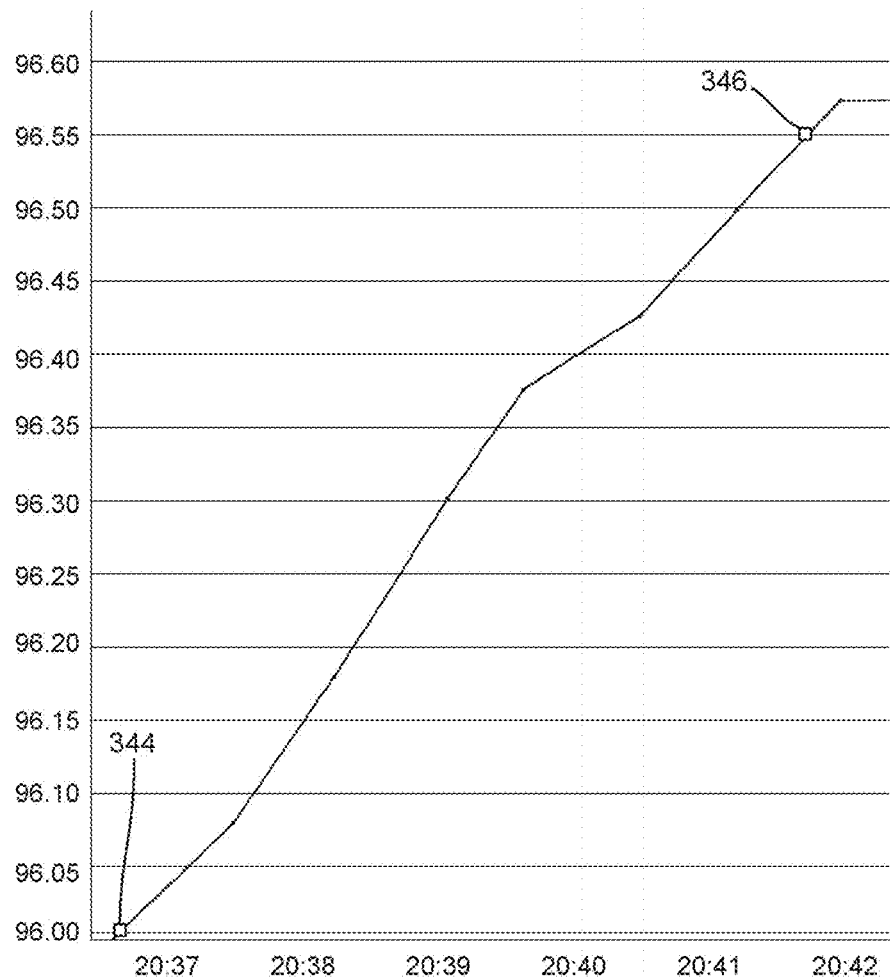
FIG. 10B shows a temperature curve representing the temperature data obtained by the incontinence care apparatus shown in FIG. 3 for detecting occurrence of voiding events, according to yet some alternative embodiments.

For example, in some embodiments as shown in FIG. 10A, a voiding event may be determined when the temperature value rises about 0.5° F. within 3 minutes (rising from point 344 to point 346 in FIG. 10A). In some other embodiments as shown in FIG. 10B, a voiding event may be determined when the temperature value rises about 0.5° F. within 5 minutes (from point 348 to point 350 in FIG. 10B).

As another example, in some embodiments, the temperature sensor module 212 has a sampling rate of one (1) sample per 30 seconds and a temperature resolution of 0.036° F. Therefore, the threshold temperature rate may be 0.1° F. per 30 seconds. In other words, a voiding event is determined and an audible alarming signal is generated when the temperature rises for at least 0.1° F. within 30 seconds.

In above embodiments, the incontinence care apparatus 204 comprises a heat-conductive strip 206 extending from a front end 140 of the cushion block 202 to a rear end 142 thereof. In some alternative embodiments, the incontinence care apparatus 204 comprises a heat-conductive plate about a central area of the cushion block 202. The heat-conductive plate may be in any suitable shape such a circle, an ellipse, square, rectangle, triangle, or the like. In some alternative embodiments, the incontinence care apparatus 204 may not comprise any heat-conductive strip or plate. Rather, the temperature sensor module 212 comprises a heat-conductive component thereon for temperature measuring.

In above embodiments, the incontinence care apparatus 204 only comprises one temperature sensor module 212. In some alternative embodiments, the incontinence care apparatus 204 may comprise a plurality of temperature sensor modules 212 arranged at different locations of the cushion block 202 for detecting voiding events with improved accuracy.

Although in some of above embodiments, an acoustic buzzer is used as the alarm module 216, in other alternative embodiments, the alarm module 216 may use any other suitable alarming means such as visual alarms, a combination of acoustic and visual alarms, and the like.

In above embodiments, the incontinence care apparatus 204 comprises a power switch for manually turning on/off the power thereof. In some alternative embodiments, the incontinence care apparatus 204 comprises a pressure switch embedded in the cushion block 202 for automatically turning on the incontinence care apparatus 204 when a care-receiver sits on the seat 132 and automatically turning off the incontinence care apparatus 204 when the care-receiver is removed from the seat 132.

In some alternative embodiments, the incontinence care apparatus 204 comprises a pressure sensor module embedded in the cushion block 202 for detecting whether or not a care-receiver is on the cushion block. In these embodiments, the incontinence care apparatus 204 is turned on when the pressure sensor module outputs a pressure measurement, which represents the weight of the care-receiver, greater than a threshold weight, for example such as 80 pounds, and is set to a sleep mode when the pressure sensor module's output is less than the threshold weight for a predetermined period of time such as 30 minutes.

In these embodiments, the pressure sensor module may also be used for determining change events. For example, a change event is determined when the pressure measured by the pressure sensor module, which represents the weight of the care-receiver, drops or reduces for a threshold pressure such as about 20 pounds for about 3 minutes. In some alternative embodiments, a change event is determined when the pressure sensor module's output drops for a threshold pressure such as about 10 pounds for about 3 minutes.

Figure 11:
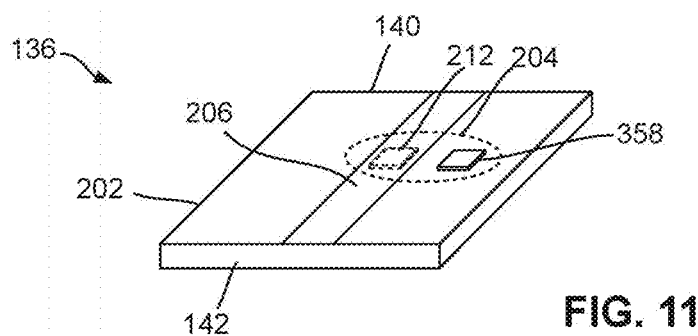
FIG. 11 shows a seat cushion of the assistive device shown in FIG. 2 according to still some alternative embodiments, wherein the seat cushion comprises an incontinence care apparatus.
Figure 12:
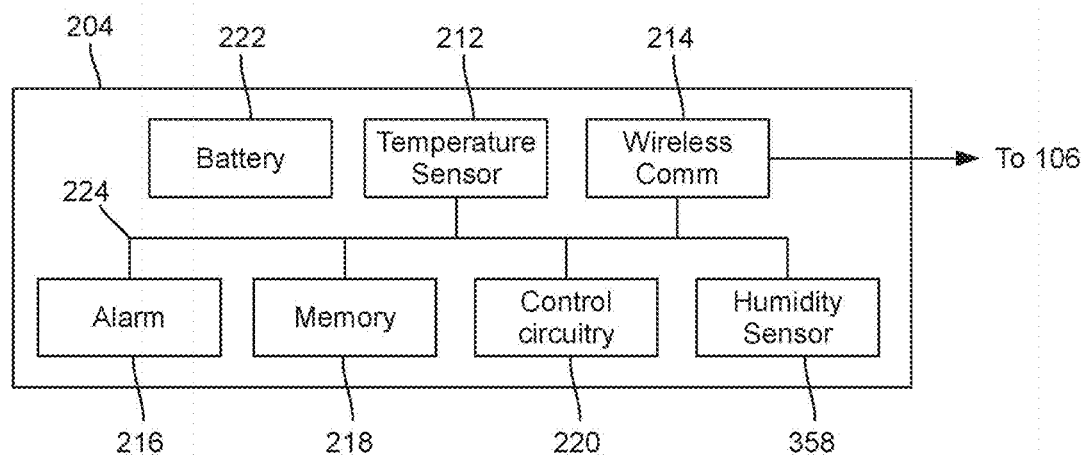
FIG. 12 is a schematic diagram showing the functional structure of the incontinence care apparatus shown in FIG. 11.

In some alternative embodiments as shown in FIG. 11, the incontinence care apparatus 204 may also comprise a humidity sensor module 358. The humidity sensor 358 may be installed above the water-proof cover of the cushion block 202 for promptly sensing humidity changes. FIG. 12 shows the functional structure of the incontinence care apparatus 204 in these embodiments.

In some embodiments, the humidity sensor module 358 is operable at least between 15° C. and 40° C., and may measure relative humidity within 0.01% resolution.

Figure 13:
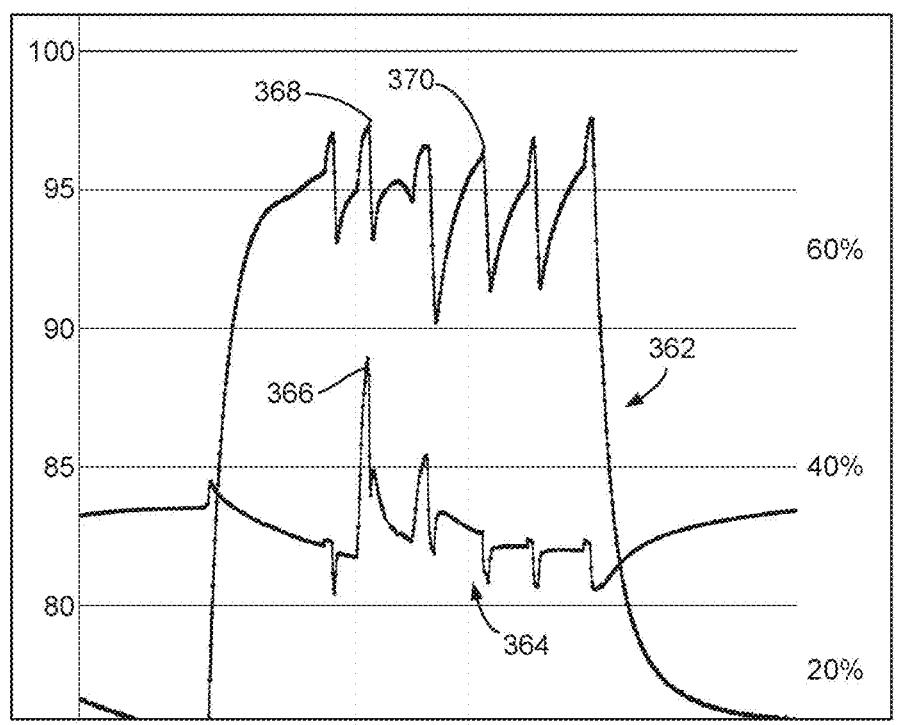
FIG. 13 shows a temperature curve and a humidity curve representing the temperature data and the humidity data recorded by the incontinence care apparatus for detecting occurrence of voiding events, according to some alternative embodiments.

In some embodiments, the humidity sensor module 358 may be used to detect a leak event. A care-receiver may be provided with protective underwear such as TENA® briefs (TENA is a registered trademark of SCA Hygiene Products AB Corp., Goteburg, Sweden) which prevents moisture from escaping therefrom. However, if a severe or voluminous voiding event occurs, the protective underwear may leak. For example, FIG. 13 shows a temperature curve 362 and a humidity curve 364 for a care-receiver wearing a TENA® brief. As the TENA® brief insulates moisture, the humidity curve 364 only exhibits small variations except a peak 366 occurred at about 12:48, about 5 minutes after the occurrence of a temperature peak 368 representing avoiding event. The humidity peak 366 corresponds to a leak from the TENA® brief, and may be detected by the humidity sensor module 358 thereby detecting a leak event.

The humidity sensor module 358 may also be a supplementary means for detecting voiding event when a care-receiver has been moved to an assistive device 102 only for a short period of time and the measured temperature has not risen to the baseline temperature range.

The temperature sensor module 212 may cause false voiding-event detection in some situations. For example, the curve 362 shown in FIG. 13 comprises a temperature peak 370 which was caused by the care-receiver's warmer-than-normal body temperature (for example, the care-receiver was removed from the assistive device 102 for a bath (leading to a warmer-than-normal body temperature) and was then moved back thereonto). In some embodiments, such a temperature peak 370 may cause a false voiding-event detection.

As can be seen in FIG. 13, the measured temperature rises to the peak 370 at a relatively slow rate. Therefore, the temperature peak 370 may be excluded and a false voiding-event detection may be prevented by applying a suitable threshold of the temperature-rising rate in the detection of voiding events.

Figure 14:
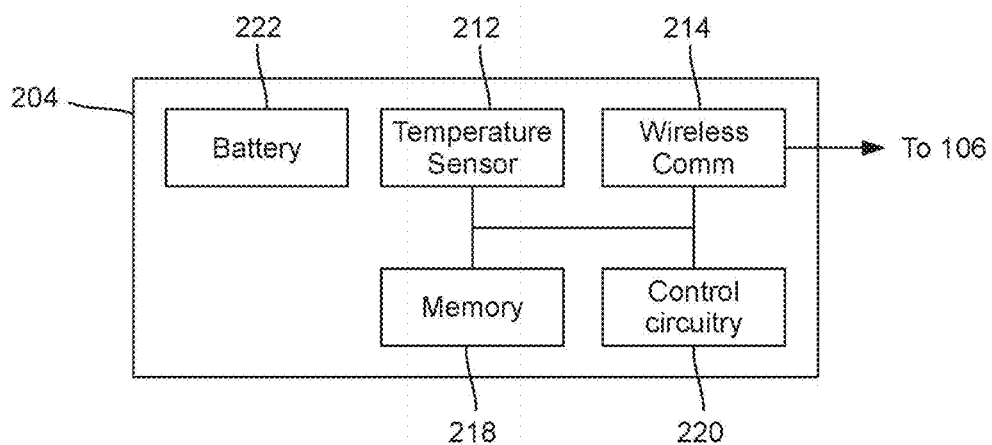
FIG. 14 is a schematic diagram showing the functional structure of the incontinence care apparatus, according to some alternative embodiments.

In some alternative embodiments, the incontinence care apparatus 204 does not comprise any alarm. FIG. 14 shows the functional structure of the incontinence care apparatus 204. In these embodiments, each caregiver carries a client computing device 114 such as a smartphone for receiving voiding event notifications. Of course, those skilled in the art will appreciate that the incontinence care apparatus 204 may also comprise other sensor modules such as a pressure sensor module and/or a humidity sensor module, as described above.

In some embodiments where the incontinence care apparatus 204 does not comprise any alarm, the incontinence care apparatus 204 does not determine any voiding events. Rather, the incontinence care apparatus 204 transmits the measured temperatures to the server computer 112. The server computer 112 determines voiding events in real time as described above, and sends voiding event notifications to the client computing devices 114 to notify the caregivers.

In above embodiments, the incontinence care apparatus 204 comprises an alarm module 216 for generating an audible alarming signal for notifying the nearby caregiver that a voiding event has occurred. In some alternative embodiments, one or more assistive devices 102 may also comprise a visible alarming component installed at a visible location of the assistive device 102 and in wired or wireless communication with the incontinence care apparatus 204. When a voiding event is detected, the visible alarming component emits a visual alarm such as flashing red light for notifying caregivers that a voiding event has occurred. The visible alarming component may be automatically turned off after a change event is detected.

Figure 15A:
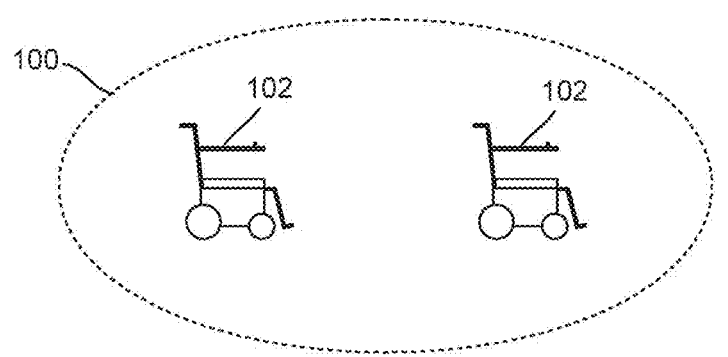
FIG. 15A is a schematic diagram showing an incontinence care system, according to some alternative embodiments.
Figure 15B:
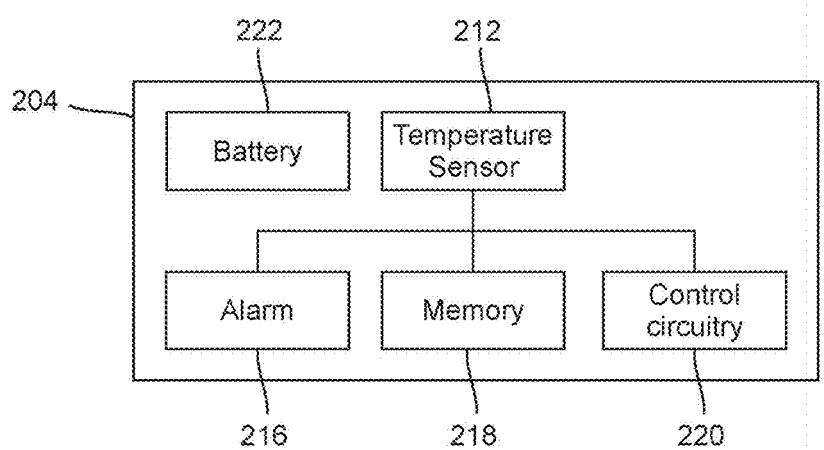
FIG. 15B is a schematic diagram showing the functional structure of the incontinence care apparatus of the incontinence care system shown in FIG. 15A.

In some alternative embodiments as shown in FIG. 15A, the system 100 only comprises one or more assistive devices 102. Each assistive device 102 is equipped with an incontinence care apparatus 204. Correspondingly, the incontinence care apparatus 204 does not comprise any wireless communication modules. FIG. 15B shows the functional structure of the incontinence care apparatus 204 in these embodiments. Of course, those skilled in the art will appreciate that the incontinence care apparatus 204 may also comprise other sensor modules such as a pressure sensor module and/or a humidity sensor module, as described above.

The incontinence care system 100 disclosed herein is suitable for use in health service facilities such as hospitals, short-term care homes, long-term care homes, in the care-receivers' homes, and the like. The incontinence care apparatuses 204 may be coupled to any suitable assistive devices 102 such as wheelchairs, beds, unmovable chairs, regular chairs, stools, disposable underwear, washable/reusable underwear, and the like.

The incontinence care system 100 facilitates the provision of timely care to care-receivers thereby reducing the risk of ailments associated with prolonged sitting in a urine-soaked undergarments. The incontinence care system 100 disclosed herein and in particular, the incontinence care apparatus 204 embedded in the wheelchair seat 132, requires minimal maintenance from caregivers. The incontinence care system 100 is easy to use and provides convenience of voiding event monitoring by providing prompt alert to caregivers when a voiding event occurs.

The incontinence care system 100 eliminates the need for fixed undergarment change schedules and facilitates the provision of personal care as needed, thereby resulting in a healthier environment for care-receivers and more efficient use of caregivers' time and resources. Test results show that the incontinence care system 100 has a success rate (i.e., the rate of correct voiding event detection) of about 91% and up to 99% in most cases.

Although in above embodiments, the temperature is measured using Fahrenheit degrees, in some alternative embodiments, the temperature may be measured using Celsius degrees (° C.). In some embodiments, a user may choose to use the Fahrenheit degrees, the Celsius degrees, or both.

Although embodiments have been described above with reference to the accompanying drawings, those of skill in the art will appreciate that variations and modifications may be made without departing from the scope thereof as defined by the appended claims.

What is claimed is:

1. A method of detecting a voiding event of a care-receiver, the method comprising:
a temperature-measurement step wherein one or more temperatures are measured in real-time at a location adjacent a lower portion of the care-receiver's torso where the voiding event is to occur; and
a voiding-determination step wherein a determination of the voiding event occurs if the measured one or more temperatures rise at a variation rate greater than or equal to a temperature-rising rate-threshold,
wherein the temperature-rising rate-threshold is about 0.5° F. per three minutes or about 0.5° F. per five minutes.

2. The method of claim 1, wherein said voiding- determination step comprises:
determining the voiding event if the measured one or more temperatures rise above an upper boundary of a predefined temperature range at the variation rate greater than or equal to the temperature-rising rate-threshold.

3. The method of claim 1, further comprising:
determining a change event if the measured one or more temperatures drop at a rate greater than or equal to a temperature-drop rate-threshold or if the measured one or more temperatures drop subsequent to the voiding event and at a rate greater than or equal to a temperature-drop rate-threshold.

4. The method of claim 3, wherein the temperature-drop rate-threshold is about 1° F. per three minutes.

5. The method of claim 1, further comprising:
determining a weight reduction; and
determining a change event if the determined weight reduction is greater than or equal to a weight-drop threshold.

6. The method of claim 1, further comprising:
measuring a weight; and
starting said temperature-measurement step if the weight measurement is greater than a weight threshold.

7. The method of claim 1, further comprising at least one of:
transmitting the measured one or more temperatures to a remote computing device; and
if the voiding event is determined, transmitting the determined voiding event to the remote computing device.

8. The method of claim 1, further comprising:
measuring a humidity; and
determining a leak event if the measured humidity is greater than or equal to a humidity threshold.

9. An apparatus for detecting a voiding event of a care-receiver, said apparatus comprising:
a heat-conductive component locatable at a location adjacent a lower portion of the care-receiver's torso where the voiding event is to occur;
a temperature sensor module coupled to the heat-conductive component for measuring one or more temperatures in real-time;
a controlling circuitry coupled to the temperature sensor; and
a power source for powering the temperature sensor module and the controlling circuitry,
wherein the controlling circuitry is configured for
a receiving-temperature-measurement step: receiving the one or more temperatures measured by the temperature sensor, and
a voiding-determination step: determining the voiding event if the measured one or more temperatures rise at a variation rate greater than or equal to a temperature-rising rate-threshold, and
wherein the temperature-rising rate-threshold is about 0.5° F. per three minutes or about 0.5° F. per five minutes.

10. The apparatus of claim 9, wherein said temperature sensor module comprises the heat-conductive component.

11. The apparatus of claim 9, wherein said heat-conductive component is a heat-conductive strip or heat-conductive plate separated from and coupled to the temperature sensor module.

12. The apparatus of claim 9, wherein said voiding-determination step comprises:
determining the voiding event if the measured one or more temperatures rise above an upper boundary of a predefined temperature range at the variation rate greater than or equal to the temperature-rising rate-threshold.

13. The apparatus of claim 9, wherein the controlling circuitry is further configured for:
determining a change event if the measured one or more temperatures drop at a rate greater than or equal to a temperature-drop rate-threshold or if the measured one or more temperatures drop subsequent to the voiding event and at a rate greater than or equal to a temperature-drop rate-threshold.

14. The apparatus of claim 13, wherein the temperature-drop rate-threshold is about 1° F. per three minutes.

15. The apparatus of claim 9, further comprising a pressure sensor module; and wherein the controlling circuitry is further configured for:
determining a weight reduction using the pressure sensor module; and
determining a change event if the determined weight reduction is greater than or equal to a weight-drop threshold.

16. The apparatus of claim 9, further comprising a pressure sensor module; and wherein the controlling circuitry is further configured for:
measuring a weight using the pressure sensor module; and
instructing the temperature sensor module to measure the one or more temperatures if the weight measurement is greater than a weight threshold.

17. The apparatus of claim 9, further comprising a wireless communication module; and wherein the controlling circuitry is further configured for using the wireless communication module for at least one of:
transmitting the measured one or more temperatures to a remote computing device; and
if the voiding event is determined, transmitting the determined voiding event to the remote computing device.

18. The apparatus of claim 9, further comprising:
a water-proof cover; and
a heat-conductive strip coupled to the temperature sensor module and extending to a location of the cover for positioning adjacent the lower portion of the care-receiver's torso where the voiding event is to occur.

19. The apparatus of claim 9, further comprising a humidity sensor module; and wherein the controlling circuitry is further configured for:
measuring a humidity; and determining a leak event if the measured humidity is greater than or equal to a humidity threshold.

20. A system for detecting a voiding event of a care-receiver, comprising:
a detection apparatus; and
a computing device coupling to the detection device via at least a wireless network,
wherein said detection apparatus comprises
   a heat-conductive component locatable at a location adjacent a lower portion of the care-receiver's torso where the voiding event is to occur,
   a temperature sensor module for measuring one or more temperatures in real-time,
   a wireless communication module,
   a controlling circuitry coupled to the temperature sensor, and
a power source for powering the temperature sensor module, the wireless communication module and the controlling circuitry, wherein the controlling circuitry is configured for
   a receiving-temperature-measurement step: receiving the one or more temperatures measured by the temperature sensor, and
   a transmitting-temperature-measurement step: transmitting the measured one or more temperatures to the computing device, wherein the computing device is configured for a voiding-determination step wherein a determination of the voiding event occurs if the measured one or more temperatures rise at a variation rate greater than or equal to a temperature-rising rate-threshold, and wherein the temperature-rising rate-threshold is about 0.5° F. per three minutes or about 0.5° F. per five minutes.

* * * * *